United States Patent
Patel et al.

(10) Patent No.: US 9,968,238 B2
(45) Date of Patent: May 15, 2018

(54) APPARATUS FOR SANITIZING AND CLEANING SOLES OF FEET AND FOOTWEAR

(71) Applicants: Kamal R. Patel, Naperville, IL (US); Sonal Patel, Naperville, IL (US)

(72) Inventors: Kamal R. Patel, Naperville, IL (US); Sonal Patel, Naperville, IL (US)

(*) Notice: Subject to any disclaimer, the term of this patent is extended or adjusted under 35 U.S.C. 154(b) by 728 days.

(21) Appl. No.: 14/473,827

(22) Filed: Aug. 29, 2014

(65) Prior Publication Data
US 2015/0096597 A1    Apr. 9, 2015

Related U.S. Application Data

(60) Provisional application No. 61/887,537, filed on Oct. 7, 2013.

(51) Int. Cl.
*A47K 3/022*    (2006.01)
*A47L 23/26*    (2006.01)

(52) U.S. Cl.
CPC ......... *A47L 23/266* (2013.01); *A61L 2202/26* (2013.01)

(58) Field of Classification Search
USPC ............................................................ 4/622
See application file for complete search history.

(56) References Cited

U.S. PATENT DOCUMENTS

| | | |
|---|---|---|
| 4,425,677 A | 1/1984 | Cox |
| 4,866,805 A | 9/1989 | Oden |
| 4,922,578 A | 5/1990 | Miettinen |
| 5,071,628 A | 12/1991 | Alazet |
| 5,297,309 A | 3/1994 | Rotoli |
| 5,792,712 A | 8/1998 | Hori |
| 5,820,821 A | 10/1998 | Kawagoe |
| 5,950,269 A | 9/1999 | Openshaw |
| 6,146,588 A | 11/2000 | Deighton |
| 6,557,203 B2 | 5/2003 | Meshbesher |
| 6,651,288 B1 | 11/2003 | Hackett |
| 6,668,842 B1 * | 12/2003 | Wilke .................. A47L 23/263 134/113 |
| 6,749,918 B2 | 6/2004 | Staal |
| 6,886,210 B2 | 5/2005 | Dean |
| 7,024,721 B2 | 4/2006 | McKay |
| 8,209,811 B2 | 7/2012 | Jordan |
| 8,241,565 B1 | 8/2012 | Abdul |
| 8,277,741 B2 | 10/2012 | McCabe |
| 8,343,434 B2 | 1/2013 | Hyde |
| 8,533,888 B2 | 9/2013 | Kessler |

(Continued)

*Primary Examiner* — Lauren Crane

(74) *Attorney, Agent, or Firm* — Chicago IP Law; Steven M. Evans

(57) ABSTRACT

An apparatus for automatically cleaning and sanitizing soles of bare feet and footwear, said apparatus including a plurality of nozzle heads that spray cleaning and sanitizing fluid through a platform onto feet and footwear placed on the top surface of the platform. A sensor plate initiates the cleaning and sanitization process when activated, and a visual display and audible tones alert a user as to the current step being executed by the automated cleaning apparatus. A refillable or replaceable canister or aerosol can of cleaning and sanitizing fluid is housed within the automated cleaning apparatus for supplying said liquid via a tubing system to the plurality of nozzle heads that are directed onto the platform.

20 Claims, 29 Drawing Sheets

(56) References Cited

U.S. PATENT DOCUMENTS

| | | |
|---|---|---|
| 8,617,464 B2 | 12/2013 | Kerr |
| 8,770,140 B2 * | 7/2014 | Nielsen .................. 118/663 |
| 8,844,584 B1 * | 9/2014 | Haley ............... B65B 31/003 141/20 |
| 2003/0029477 A1 | 2/2003 | Dean |
| 2004/0078909 A1 | 4/2004 | Coppa |
| 2005/0160549 A1 | 7/2005 | Dean |
| 2007/0271715 A1 * | 11/2007 | Scoralle ............ A47L 23/22 15/104.92 |
| 2010/0104470 A1 | 4/2010 | McCabe |
| 2010/0193709 A1 | 8/2010 | Dalton |
| 2010/0296970 A1 | 11/2010 | Trimarco |
| 2010/0316528 A1 | 12/2010 | Jordan |
| 2012/0167325 A1 | 7/2012 | Omidi |
| 2012/0230867 A1 | 9/2012 | Kerr |
| 2013/0101461 A1 | 4/2013 | Gil |

* cited by examiner

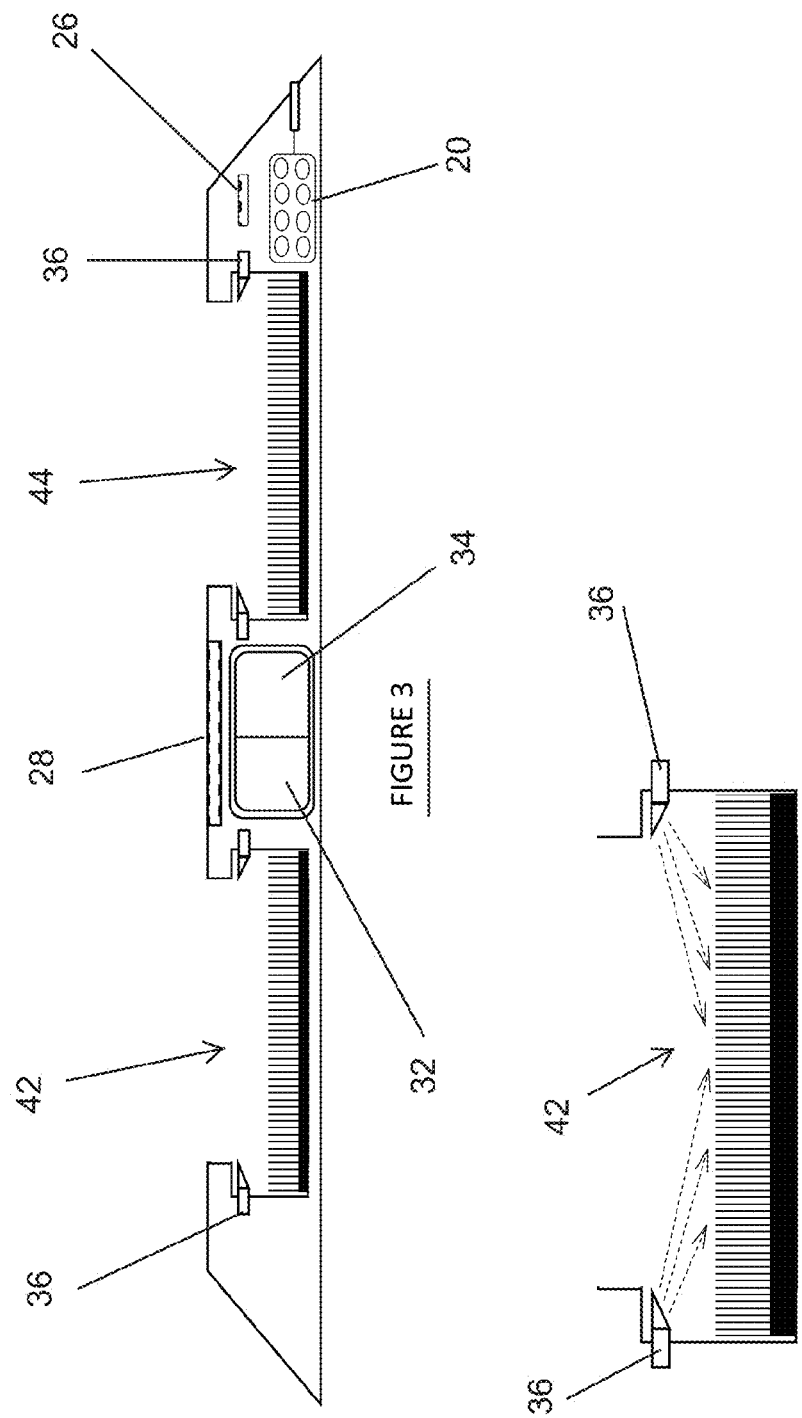

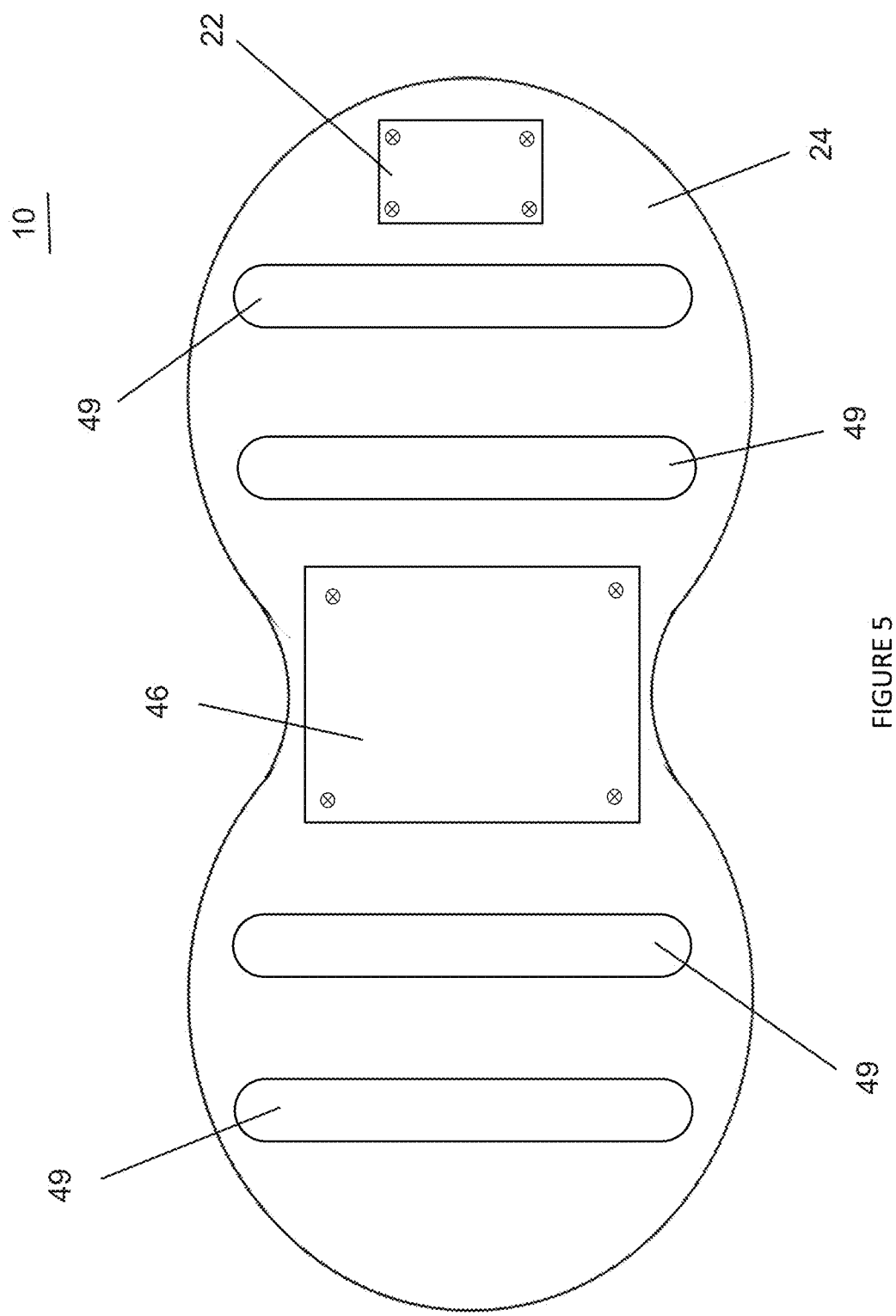

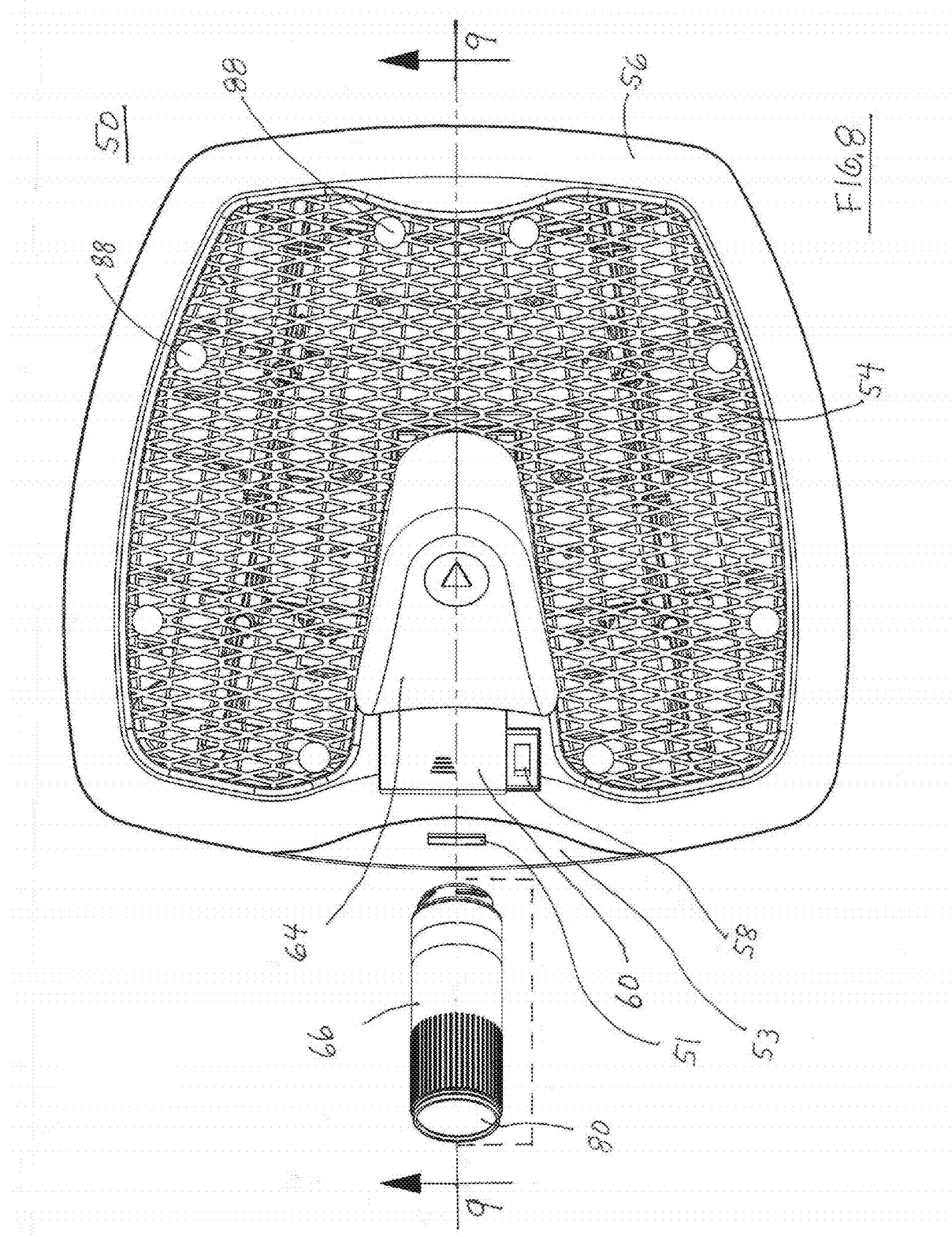

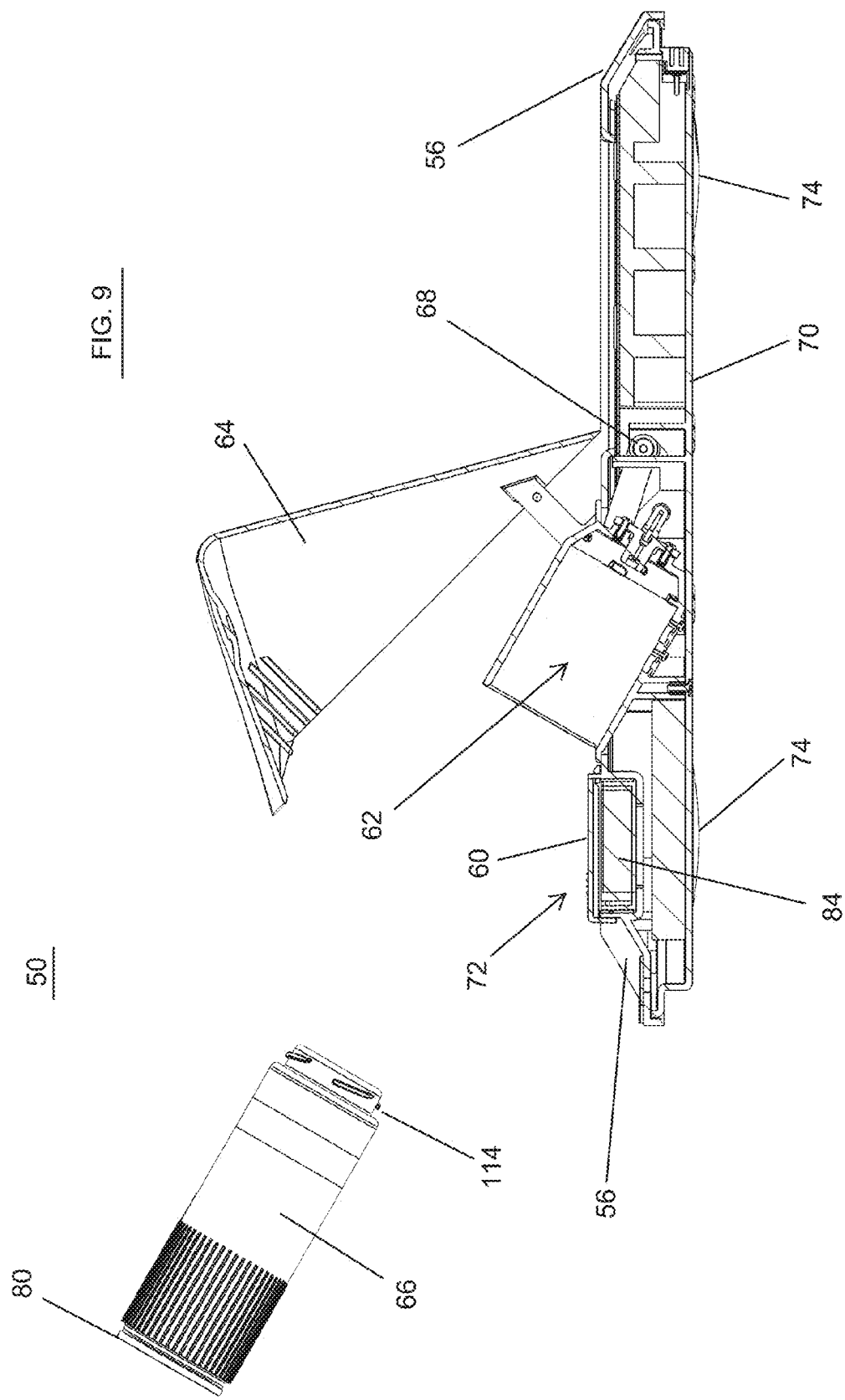

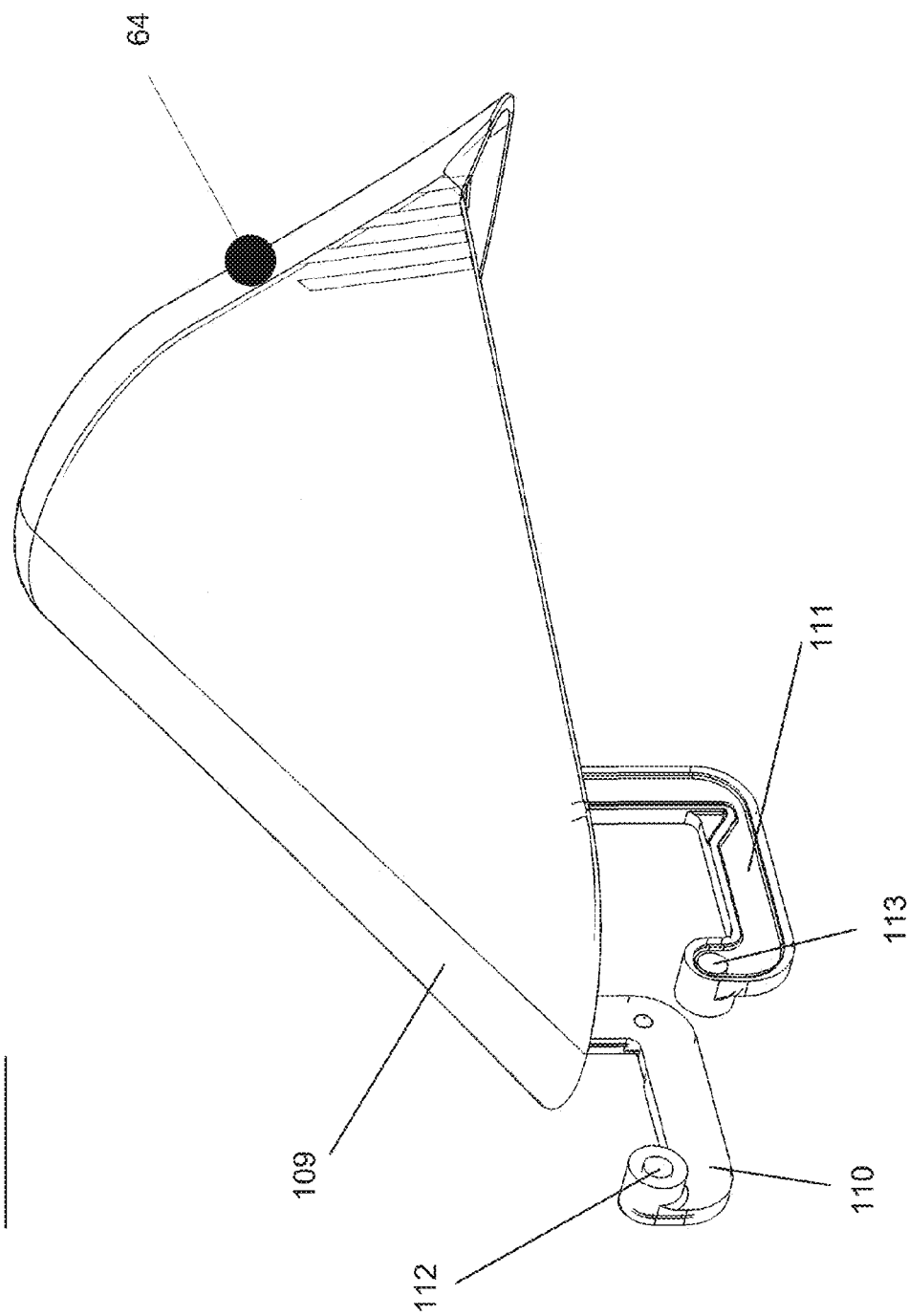

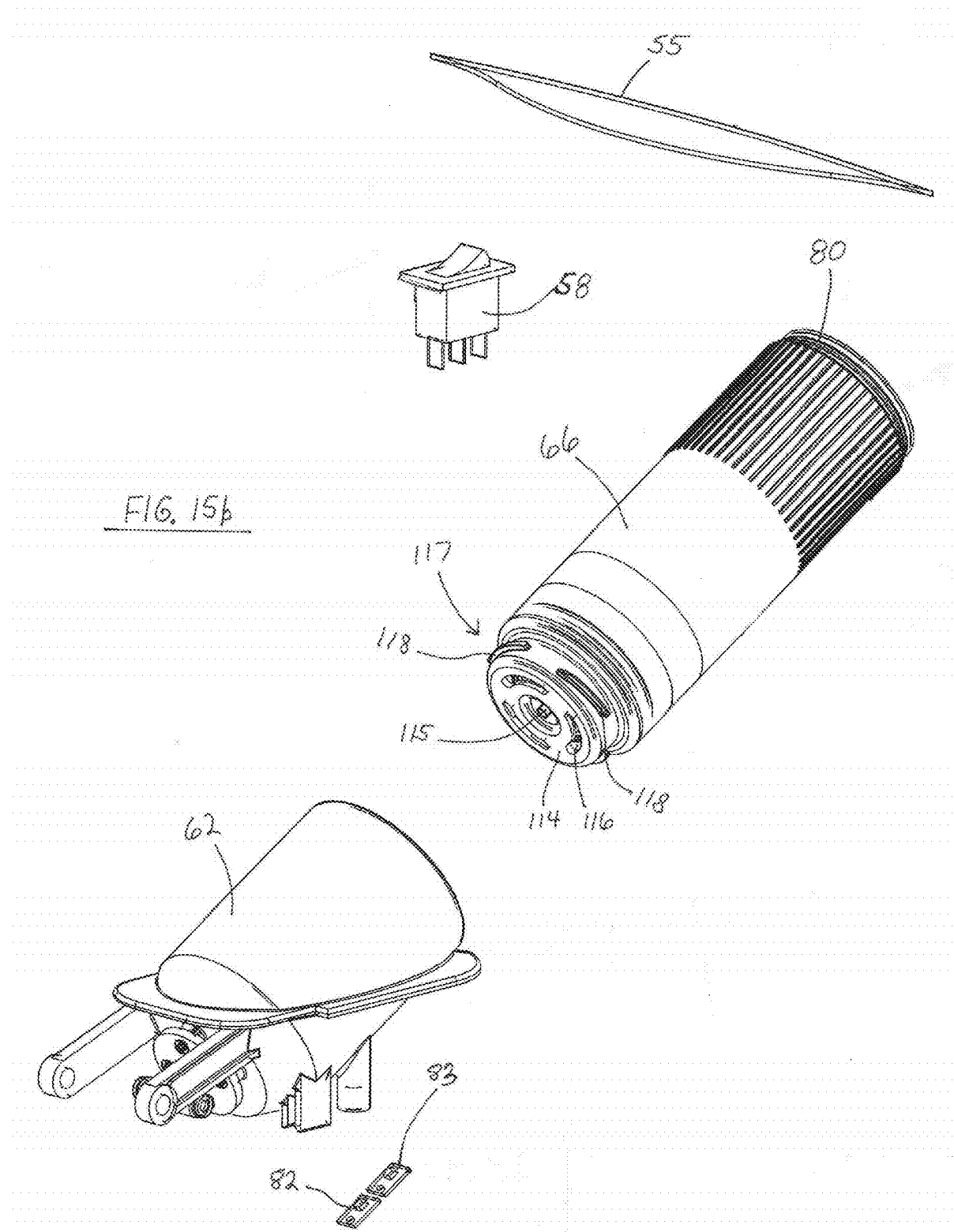

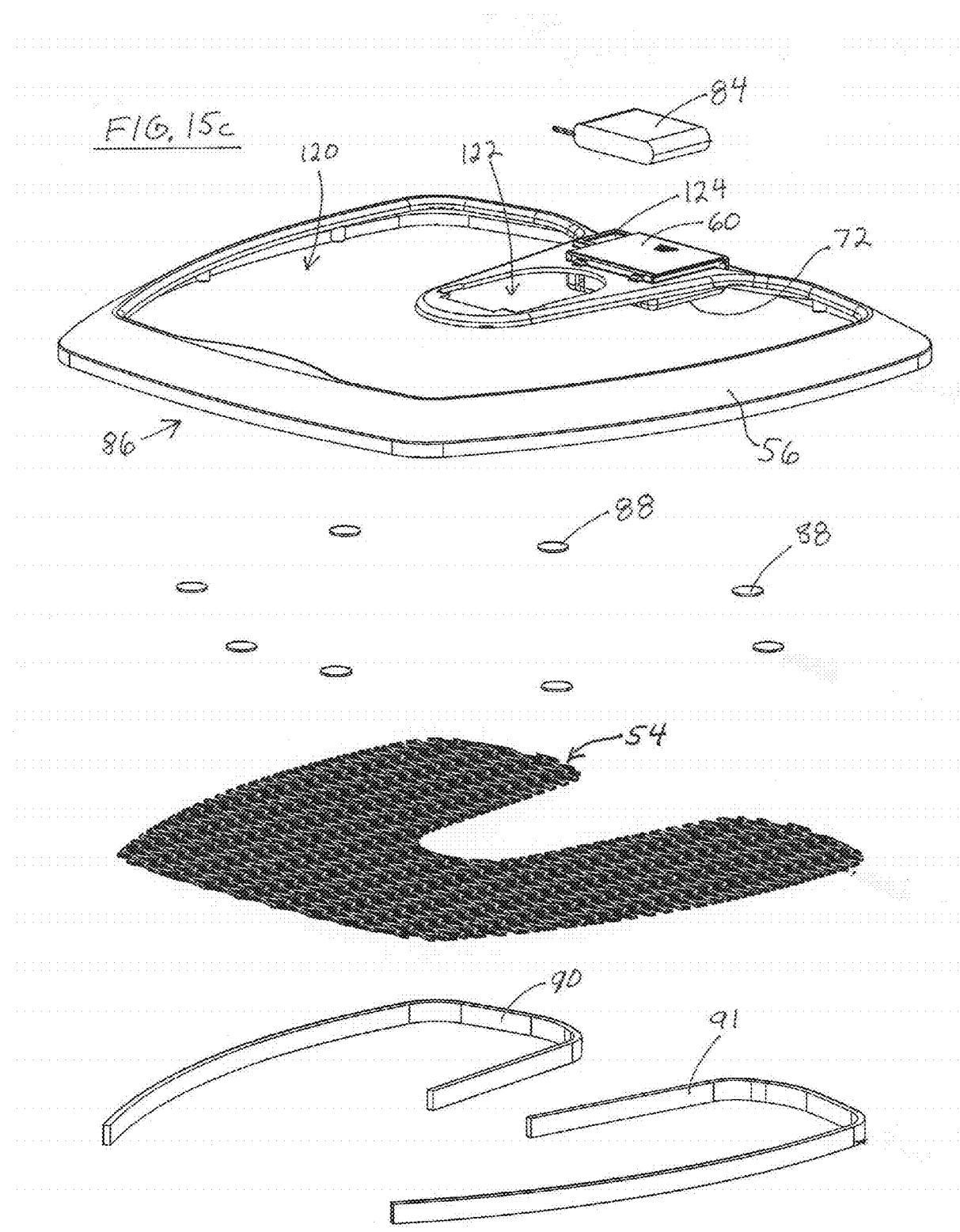

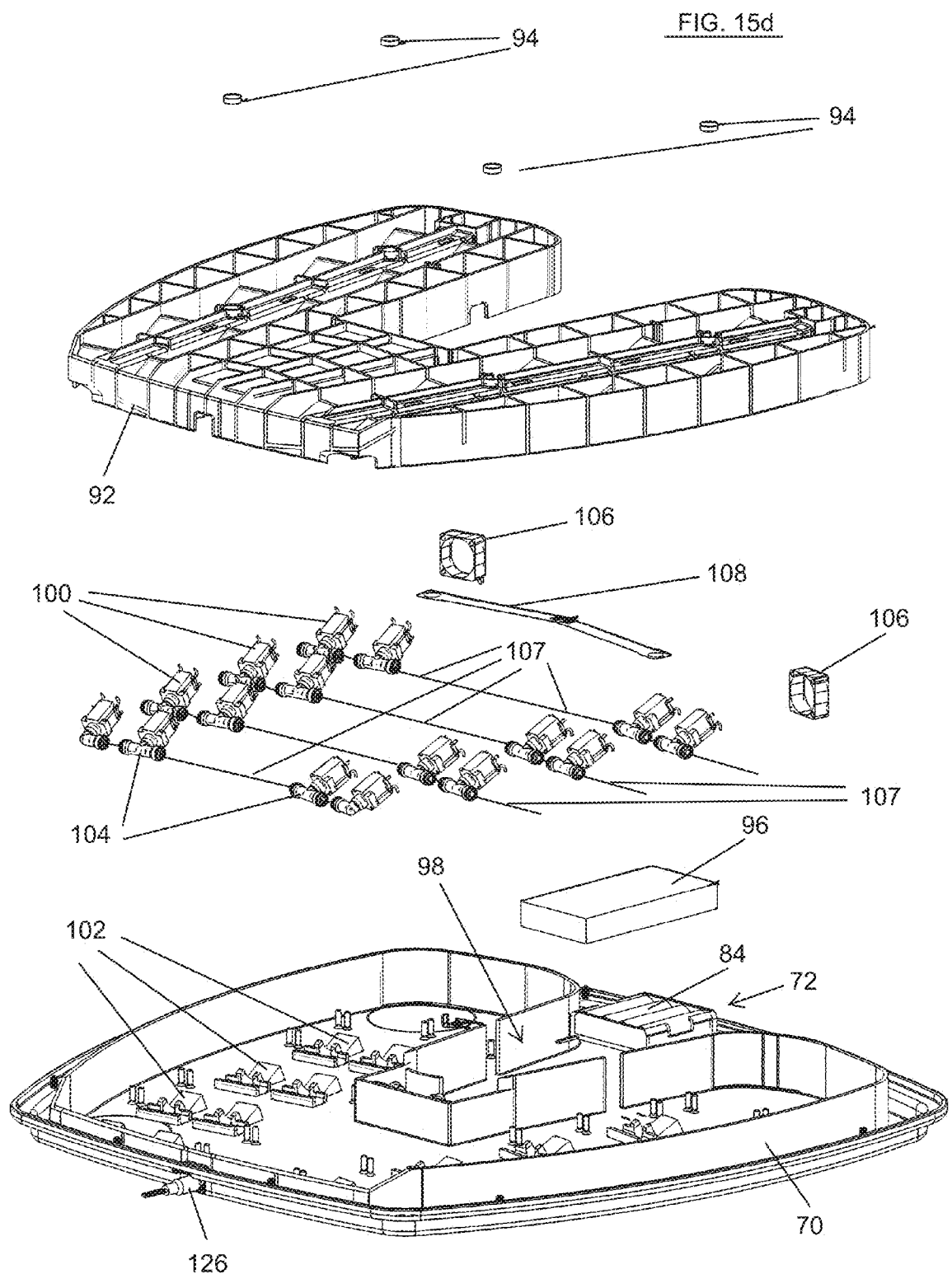

APPARATUS FOR SANITIZING AND CLEANING SOLES OF FEET AND FOOTWEAR

CROSS-REFERENCE TO RELATED APPLICATION

This non-provisional patent application claims priority and benefit of U.S. provisional patent application having application No. 61/887,537, filed on Oct. 7, 2013, and entitled "Device for the Sanitization and Cleaning of Feet and Footwear Soles," which is hereby incorporated by reference.

BACKGROUND OF THE INVENTION

Field of the Invention

The present invention relates generally to cleaning and sanitizing devices, and more particularly, to an apparatus for automatically sanitizing and cleaning soles of feet and footwear.

Description of Related Art

Doormats are commonly placed outside the doorways of homes, office buildings and businesses to remove dirt and debris from the soles of shoes prior to an individual entering into a building. Doormats or floor mats are typically simple, carpeted, bristled, and/or moisture-absorbing surfaces that collect dirt particulates and debris. People typically drag or scrap the bottom of their shoes across the floor mat to remove debris from the bottom of their shoes. Some floor mats include cleaning solution to assist in the removal of debris from the bottom of shoe shoes. While such mats are commonly used, these floor mats typically do not remove all of the debris from shoes. Moreover, such conventional mats do not sanitize shoes to prevent the spread of bacteria and viruses before entering a home or office. Furthermore, these floor mats are not designed to clean and sanitize bare feet.

During a typical day, people acquire a great deal of bacteria, germs, viruses, chemicals, toxins, and debris on the soles of their shoes. If they are wearing sandals or in bare feet, then their feet can become very dirty and contaminated as well. Surfaces such as roads, sidewalks, public areas, and yards have a high content of food waste, human and animal excrement, organic decompositions, dirt and debris. This dirt contains harmful bacteria and viruses that can potentially pose serious health risks if brought into a household or dwelling. If dirt is not removed prior to entry, the dirt can be tracked into a home or building and deposited on clean floors. Dirt left on floors results in an unclean appearance, promotes the proliferation of harmful bacteria and viruses, and can damage floors and carpeting.

Additionally, walking into a home wearing shoes or bare feet drags in unimaginable germs, bacteria, fecal matter and urine (human, animal, and insect), viruses, fungus, pollutants, vomit, allergens, saliva, rotten food, dirt and debris, pesticides and fertilizers, coal tar, lead, and other chemicals and toxins that can invade and spread throughout your home. These items can be incredibly dangerous to people's and pet's health and cause damage to areas of homes.

The dirt, debris and chemicals that are tracked into the home on shoes and feet over time can damage, dull, and stain hardwood floors and carpet. The dirt and debris slightly scratches the surface and repeatedly, over time, hardwood floors become dull. Carpets and rugs also become dirty, discolored, and damaged as the dirt, debris, and chemicals become imbedded into the fibers, and over time, becomes very difficult to remove and thoroughly clean and sanitize.

More importantly, carpets and rugs can become breeding grounds for bacteria and viruses that become imbedded into the fibers. Homeowners may vacuum rugs and carpets frequently, however, vacuuming alone cannot remove all of these items and does not kill the germs, bacteria and viruses that may exist in carpets and rugs.

These harmful items ultimately can transfer to other surfaces and items in the home including tables, sofas, chairs, and beds as residents and visitors place their shoes and feet on these items. Infants and young children spend a lot of time on the floor, and due to their size, they are naturally closer to the floor, and also may put many items that contact the floor into their mouths such as toys, stuffed animals, blankets, food, sippy cups, baby bottles, and their own hands and feet. With growing central nervous and immune systems, toxic chemicals and can be especially damaging to their health and growth. Furthermore, as infants and younger children play, crawl, and roll on the floor, any germs picked up by bare feet, knees, and hands will then be transported to their cribs at naptime and night. Children also tend to rub their eyes often which can transfer harmful items from their hands to their eyes.

According to research conducted by the University of Arizona, a myriad of dangerous and health-threatening germs are carried unknowingly on shoes. For example, the research found large amounts of deadly *Escherichia coli* (*E. Coli*); *klebsiella pneumonia*, which can cause pneumonia and wound and bloodstream infections; and *Serratia ficaria*, which can lead to infection of the respiratory tract. According to the researchers, the common occurrence of coliform and *E. coli* bacteria indicates frequent contact with fecal matter. The study also indicated (i) that bacteria can be tracked by shoes over a long distance into homes after the shoes were initially contaminated; and (ii) the transfer rate of bacteria from the shoes to uncontaminated tiles ranged from 90% to 99%—given that most home flooring includes porous wood, throw rugs and carpet; direct transmission is virtually certain; and (iii) bacteria live longer on shoes than in other places given the constant daily contact with new debris that feeds the growth of more bacteria; and (iv) shoes have more units of bacteria than toilet seats.

Conventional floor mats, after continued use, become imbedded with dirt, dust and debris that limit their usefulness when cleaning a user's feet or shoes. Furthermore, typical doormats do not sanitize shoes or feet.

Accordingly, based upon the heath and cleanliness concerns discussed above, there is a need for an apparatus that cleans and sanitizes the soles of both feet and footwear.

ASPECTS AND SUMMARY OF THE PRESENT INVENTION

One aspect of the present invention is to provide an apparatus that more effectively cleans and sanitizes the soles of both feet and footwear.

Another aspect of the present invention is to provide an apparatus that can be cleaned to prevent a buildup of dirt and debris after continued use which reduces the operational effectiveness of the apparatus.

A further aspect of the present invention is to provide an improved apparatus for cleaning the bottoms of shoes.

Another aspect of the present invention is to provide an apparatus for more effectively cleaning, sanitizing, refreshing, and deodorizing bare feet.

Another aspect of the present invention is to provide an apparatus that sanitizes in addition to cleaning shoes and bare feet.

An additional aspect of the present invention is to provide a cleaning and sanitizing apparatus that is automated in order to provide more effective and reliable cleaning and sanitizing functionality.

Another aspect of the present invention is to provide a cleaning and sanitizing apparatus that is visually attractive, portable, easy to maintain, and easy to use.

In order to achieve these aspects and others, the present invention provides an automated apparatus that cleans and sanitizes both bare feet and footwear. The present invention addresses the issue of pathogens, chemicals, toxins, and debris being tracked into the home by sanitizing, disinfecting, and cleaning the soles of shoes and sanitizing, refreshing, cleaning, and deodorizing bare feet through an automated process. The automated apparatus can be placed anywhere in a residential or commercial structure where desired.

The apparatus for automatically cleaning soles of both feet and footwear includes a base and a platform located above the base having a top surface and a bottom surface, wherein the platform enables liquid to pass therethrough. A dock connected to the base receives an aerosol can and a first plurality of spray nozzles located below the platform are configured to direct liquid from the bottom surface to the top surface. A piping network connects the dock to the first plurality of spray nozzles. A control circuit controls operation of the spray nozzles. An optical sensor connected to the dock reads an optical code on a can located with the dock to determine contents of can within the dock.

In a further embodiment the apparatus includes a bevel edge oval or similar based structure that contains two oval shaped depressions or foot/shoe receptacles a user steps into to clean and sanitize his or her bare feet or footwear. The left and right receptacles contain replaceable bristle like textile pads or similar material that cleans and sanitizes feet or shoes, and facilitates drying and evaporation of cleaning and sanitizing fluid. The receptacles are surrounded by a number of nozzle heads that spray cleaning and sanitizing fluid into the receptacle and over the textile material. The apparatus includes a sensor plate that initiates the cleaning and sanitization process when activated. The apparatus also includes an light emitting diode (LED) or similar type of display that, through a series of illuminated displays and audible tones, alerts a user as to what step the apparatus is currently on and what steps the user should take next. A refillable or replaceable canister or aerosol can of cleaning and sanitizing fluid is housed within the apparatus and the fluid is distributed and sprayed into the receptacles or depressions through a series of tubing, pumps and nozzles. The apparatus includes a power on and off switch and is powered by a rechargeable battery that can be plugged into an AC wall outlet. The underside of the apparatus includes silicon or rubber pads to prevent the apparatus from slipping, and access panels to allow for replacement of cleaning and sanitizing fluid canisters, and rechargeable batteries.

In accordance with a further embodiment of the present invention, an apparatus is provided that utilized two different sanitizing and disinfecting aerosol formulations for use on (i) soles of footwear, and (ii) bare feet. The use of two different solutions ensures efficacy and safety for the specific applications. Both formulations are readily commercially available, currently used in numerous applications, safe, tested to kill and reduce the number of germs and viruses, and approved by the EPA and FDA, respectively. Both formulations will each have their own unique scent to provide a pleasant experience for users. The formulation (i) for use on the soles of foot wear can include isopropyl alcohol and quaternary ammonium compounds as the active ingredients, which have been proven to kill and reduce the occurrence of many germs and viruses. The formulation (ii) for use on bare feet can include upwards of 65% of ethanol as the active ingredient and contain moisturizers to prevent drying of the skin.

In a further embodiment of the present invention, a single sanitizing and disinfecting aerosol formulation for use on both (i) soles of footwear and (ii) bare feet in provided. The apparatus includes a sensor, such as an optical sensor, that reads an optical code on the aerosol can providing the cleaning and disinfecting solution, and the apparatus adjust its operational procedure accordingly depending upon the contents of the aerosol can. In the third embodiment, the apparatus is designed to recognize at least three different contents of the aerosol can supplying the cleaning and disinfecting solutions: (1) a solution only for cleaning and sanitizing the soles of footwear; (2) a solution only for cleaning and sanitizing the soles of feet; and (3) a solution for cleaning and sanitizing the soles of both feet and footwear.

The foregoing has outlined, rather broadly, the preferred features of the present invention so that those skilled in the art may better understand the detailed description of the invention that follows. Additional features of the invention will be described hereinafter that form the subject of the claims of the invention. Those skilled in the art should appreciate that they can readily use the disclosed invention and specific embodiments as a basis for designing or modifying other structures for carrying out the same purposes of the present invention, and that such other structures do not depart from the spirit and scope of the invention in its broadest form.

BRIEF DESCRIPTION OF THE DRAWINGS

FIG. 3 is a cross-sectional view of the apparatus shown in and taken along line 3-3 of FIG. 1;

FIG. 4 is an enlarged view of the shoe and foot receptacle shown in FIG. 3;

FIG. 5 is a bottom view of the cleaning apparatus shown in FIG. 1;

FIG. 8 is a top view of the feet and footwear sanitizing and cleaning apparatus shown in FIG. 7, wherein a dock for an aerosol spray can is open, and an aerosol can is external to the apparatus;

FIG. 9 is a cross-sectional view of the apparatus shown in and taken along line 9-9 of FIG. 8;

FIG. 15a is an enlarged view of the dock cover of the present invention shown in FIG. 15;

FIG. 15b is an enlarged view of the on/off switch, aerosol can housing, and dock of the present invention shown in FIG. 15;

FIG. 15c is an enlarged view of the top cover, grate, and LED lighting of the present invention shown in FIG. 15;

FIG. 15d is an enlarged view of the compartmentalized support, spray nozzles, and base of the present invention shown in FIG. 15;

Other features and advantages of the present invention will become apparent to those skilled in the art from the following detailed description. It should be understood that the detailed description and specific examples, while indicating the preferred embodiment of the present invention, are given by way of illustration and not limitation. Many changes and modifications within the scope of the present invention may be made without departing from the spirit of the invention, and the invention includes all such modifications.

DETAILED DESCRIPTION OF THE PREFERRED EMBODIMENTS

Figure 1:
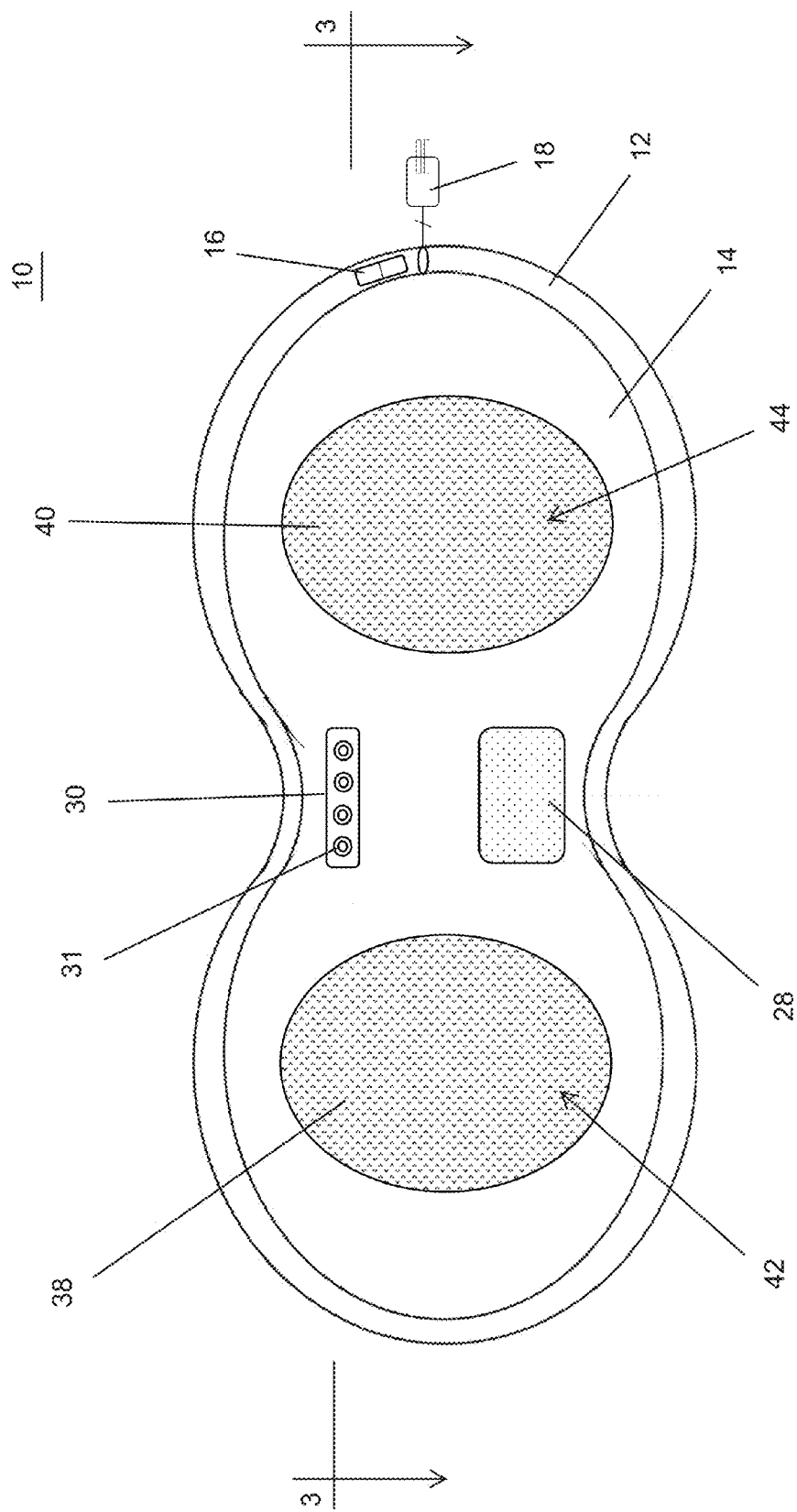
FIG. 1 is a plan view of a feet and footwear sanitizing and cleaning apparatus configured in accordance with a first embodiment of the present invention.

Turning now to the drawings, FIG. 1 is a plan view of an apparatus 10 configured in accordance with a first embodiment of the present invention. The functionality of the apparatus 10 is automated for more effective cleaning and sanitizing of both footwear and bare feet. The apparatus 10 preferably has an elliptical or figure-8 shape and is surrounded by a top cover 14 having a beveled edge 12 that slopes from a top of the apparatus 10 toward a supporting surface or floor. The apparatus 10 can be turned on and off by a power switch 16 located on the top cover 14 or along the beveled edge 12. A removable power cord 18 can be plugged into the apparatus 10 to recharge rechargeable and removable batteries 20 (FIG. 3) that are housed within the apparatus 10 and accessible by opening an access panel 22 (FIG. 5) on the underside 24 (FIG. 5) of the apparatus 10. Alternatively, the rechargeable batteries 20 can be removed by sliding them out of an access point located along the beveled edge 12 and then recharged by plugging the batteries 20 into a DC battery charger powered by a standard AC wall outlet.

The apparatus 10 is designed to be ready for use after the apparatus 10 is plugged into a standard AC wall outlet via the power cord 18 or the rechargeable battery 20 is reinserted and recharged, and the power switch 16 is activated. An electronic control board 26 (FIG. 3) coordinates processes and steps of the apparatus 10 and is connected to a sensor plate 28, the power switch 16, the rechargeable battery or batteries 20, an LED or similar type of illuminated display 30, a fluid canister 32 (FIG. 3), and a fluid distribution pump 34 (FIG. 3). The electronic control board 26 is accessed through the panel 46 (FIG. 5) located on the underside 24 of the apparatus 10.

The sequence of events to initiate and perform the sanitization and cleaning process of the apparatus 10 preferably is as follows:

A user approaches the apparatus 10 and taps the sensor plate 28 located on top 14 of the apparatus 10. The sensor plate 28 can be tapped with the user's foot or hand. After one tap, a short audible tone will be emitted from an audible source or speaker 33 (FIG. 2) of the apparatus 10, and one light 31 on the LED or similar display 30 will illuminate to signal that the apparatus 10 is ready. The user will then be required to tap the sensor plate 28 a second time to ensure that the apparatus 10 was intentionally activated. After the second tap, a longer audible tone will be emitted from the speaker 33 and a second light on the LED or similar display 30 will illuminate. If the sensor plate 28 is not tapped for the second time within a short amount of time after the first tap, the one light that is illuminated in the display 30 will turn off and the apparatus 10 will go back into sleep mode.

After the second tap, cleaning and sanitization fluid from the fluid canister or an aerosol can 32 will be sprayed from a plurality of nozzles 36 (FIGS. 3 and 4) located around the perimeter of each foot depression or receptacle 38, 40 and into the depressions 38,40 and onto bristle like textile pads 42,44 or similar material located at the base of each depression 38,40. The beveled edge 12 preferably is a different color than the top 14 of the apparatus 10 for artistic design.

After the spraying step is complete, a third audible tone will be emitted and a third light on the display 30 will illuminate signaling the user that he of she can now step into the foot depressions 38,40 either with bare feet or footwear. The user then steps into the left and right depressions 38, 40, respectively, and swipes his or her feet back and forth within the depressions 38,40 to clean and sanitize his or her shoe soles or feet. After a three to five second period of time, another audible tone will be emitted and the fourth light on the display 30 will illuminate signaling that the process has been completed and the user can step off the apparatus 10. The illuminated lights 31 in the display 30 will all flash several times and then turn off indicating the apparatus 10 is ready for the next user.

The bristle like pads or similar material 42,44 located at the base of the foot depressions 38,40 preferably are made from materials that allow for cleaning and sanitizing of the soles of footwear and feet, and facilitate the evaporation of the sanitizing and cleaning fluid. The pads 42,44 are removable and can be washed or replaced by the user as needed or desired. During the process of a user wiping his or her feet back and forth in the foot depressions 38,40, the cleaning and sanitization fluid that was sprayed on the bristle or textile pads 42,44 is transferred to the soles of the footwear or feet of the user, and the back and forth wiping motion results in the cleaning and sanitization of the soles. The back and forth wiping motion also facilitates the evaporation of the cleaning and sanitization fluid.

The two oval shaped depressions 38,40 preferably are sized to accommodate shoes of an average person wearing footwear. The foot depressions 38,40 have a plurality of spray heads or nozzles 36 (FIGS. 3 and 4) around the perimeter and located above the textile or similar pads 42,44. The spray heads or nozzles 36 are positioned so that sprayed sanitizing and cleaning fluid thoroughly moistens and covers the textile pads 42,44 to effectively clean and sanitize bare feet soles or footwear soles. The spray heads and nozzles 36 are angled in a manner that directs the sprayed sanitizing and cleaning fluid downward towards the foot depressions 38,40 and onto the textile or bristle pads 42,44. The downward facing direction of the spray heads and nozzles 36 along with the volume and pressure of the sprayed sanitizing and cleaning fluid, prevents the sprayed fluid from contacting surfaces outside of the sole depressions 38,40. The amount of sanitizing and cleaning fluid dispensed can be adjusted by the user for individual preferences by accessing controls located under the access panel 46 (FIG. 5).

Figure 2:
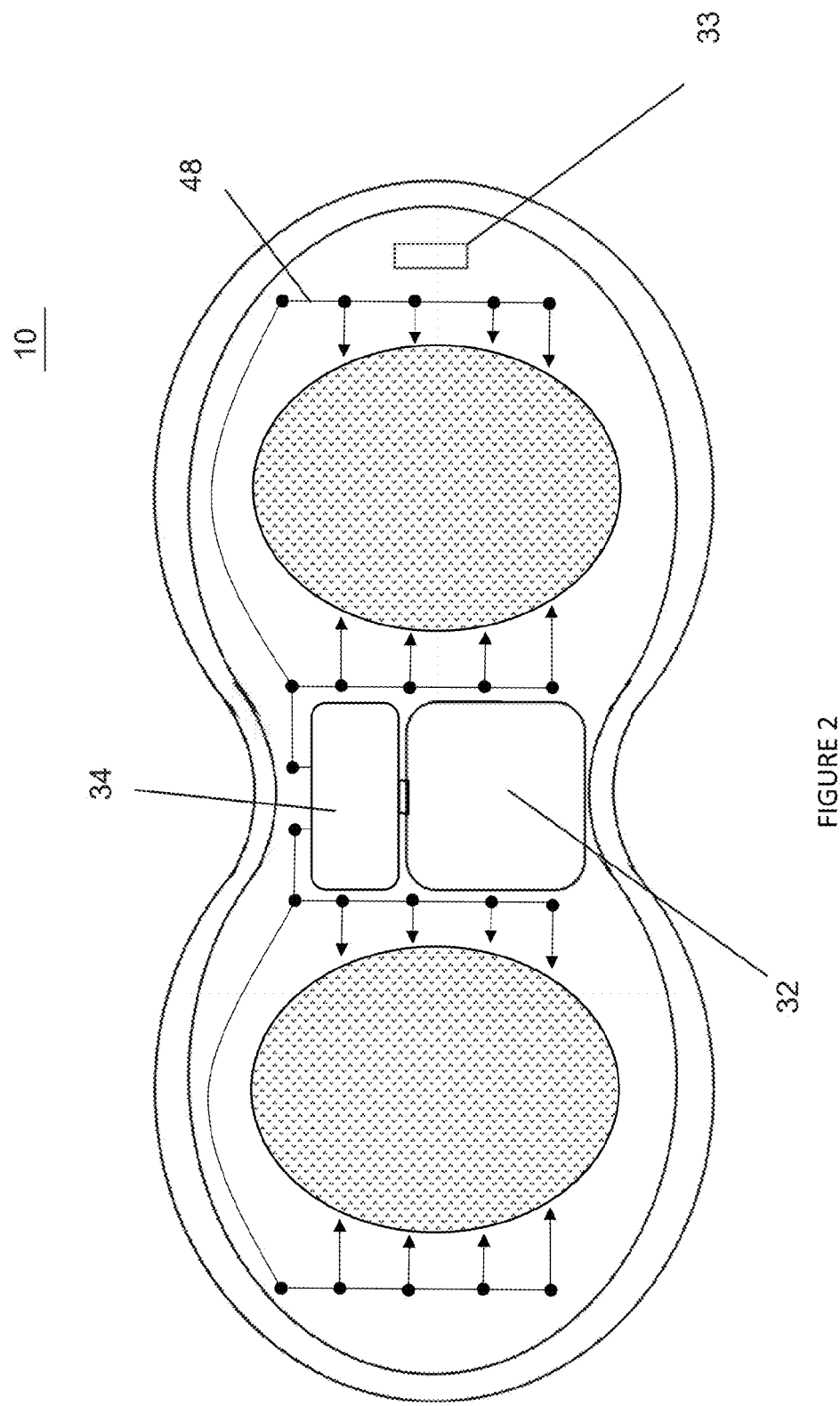
FIG. 2 is a top view of the footwear and feet sanitizing and cleaning apparatus shown in FIG. 1, wherein the top cover has been removed to expose internal components and circuitry.
Figure 6:
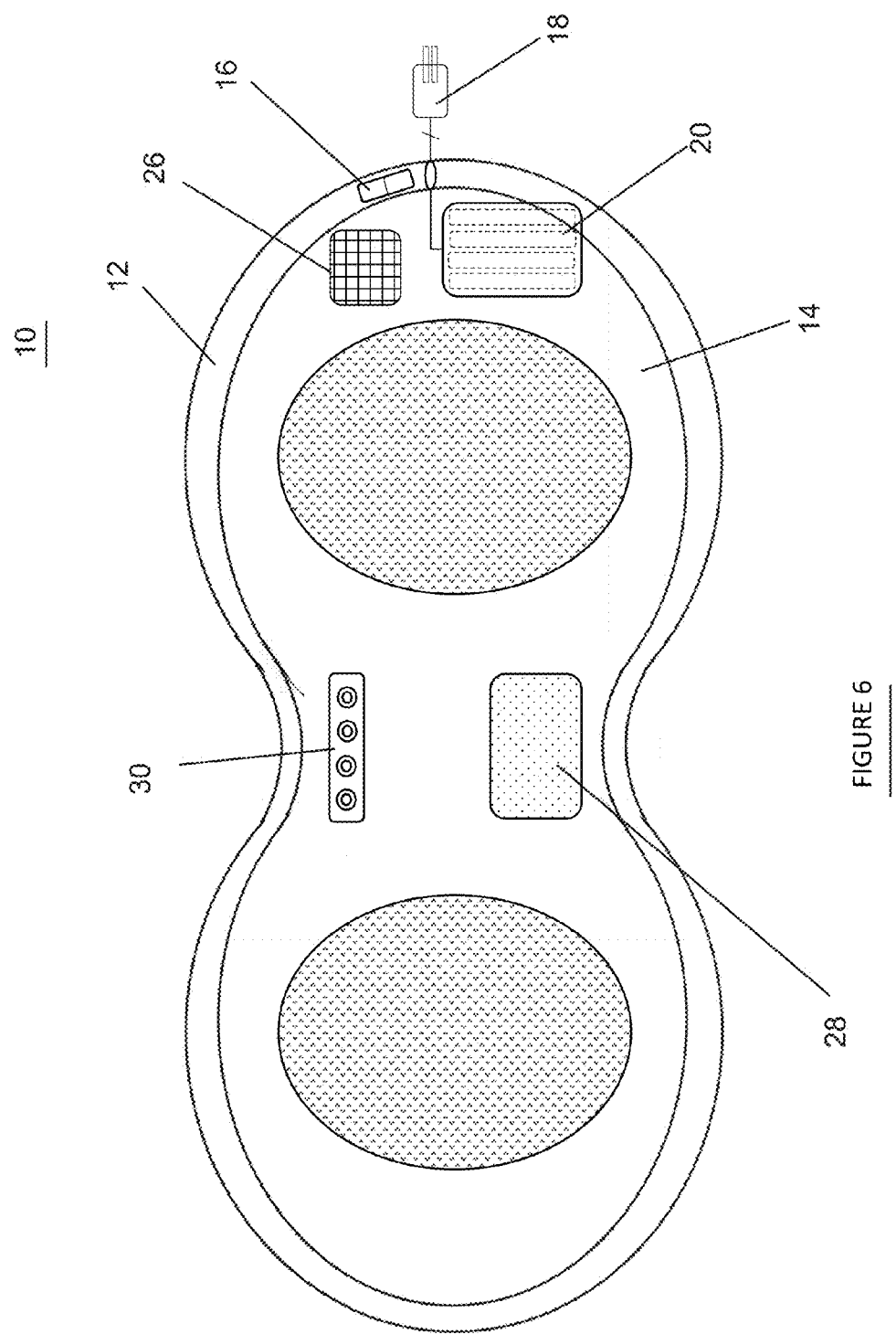
FIG. 6 illustrates additional electrical components of the cleaning apparatus shown in FIG. 1.

The sanitizing and cleaning fluid is distributed from a metal or plastic canister 32 containing such fluid to the multitude of spray heads and nozzles 36 by a series of tubes or piping system 48 (FIG. 2). A power activated pump 34 facilitates delivery of the sanitizing and cleaning fluid through the tubes or piping 48 to the spray heads or nozzles 36. The canister 32 containing the sanitizing and cleaning fluid can be pressurized to facilitate distribution of the cleaning fluid. The canister 32 is user refillable or disposable and replaceable, and accessed through the panel 46 located on the underside 24 of the apparatus 10. The underside 24 of the apparatus 10 is includes several silicone based or rubber pads 49 applied to the underside 24 to prevent the apparatus 10 from slipping or sliding along a floor or supporting surface.

Figure 7:
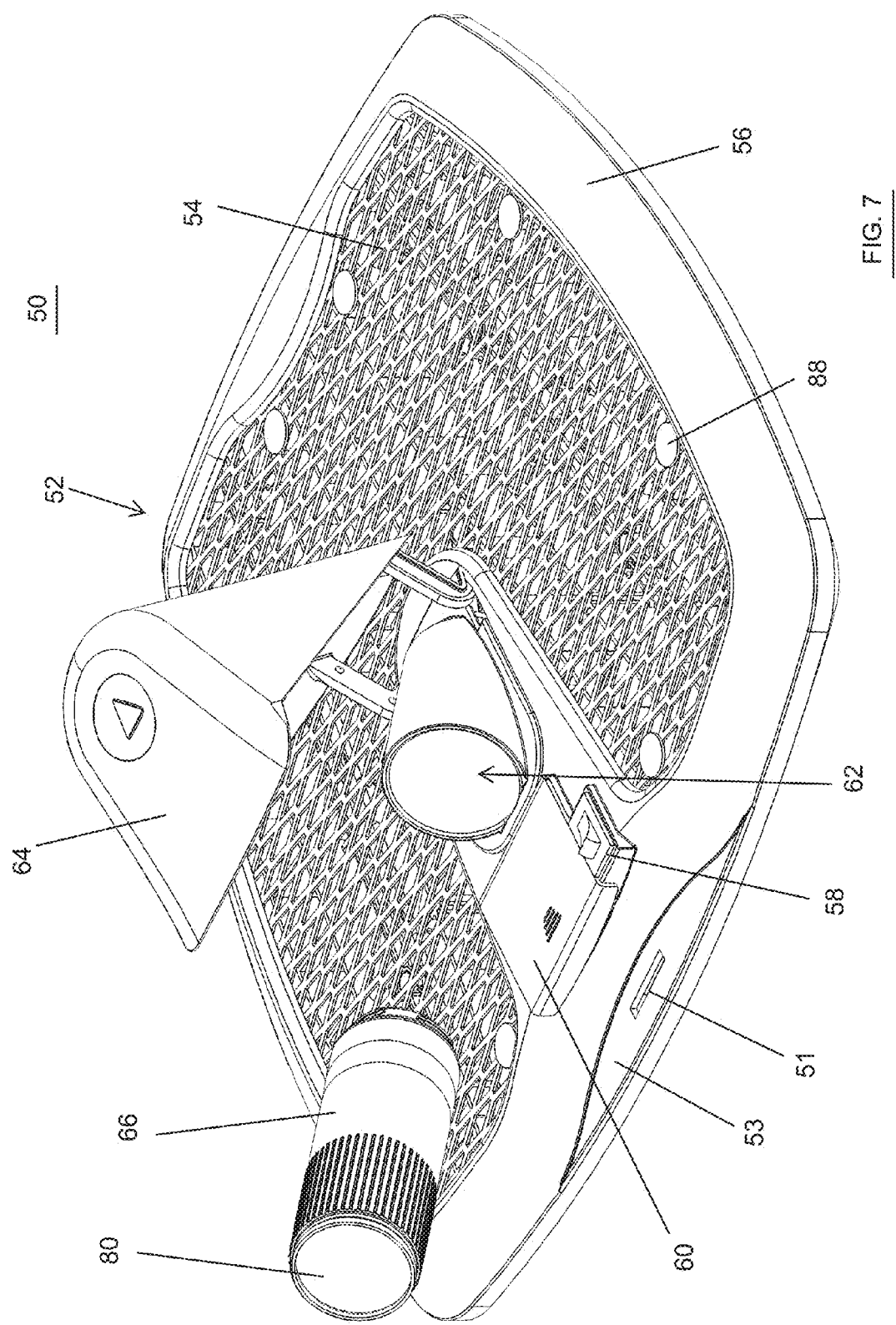
FIG. 7 is a perspective view of a feet and footwear sanitizing and cleaning apparatus configured in accordance with a second and preferred embodiment of the present invention.

FIG. 7 illustrates a perspective view of an apparatus 50 configured in accordance with a preferred and second embodiment of the present invention. The apparatus 50 preferably has a rectangular configuration with rounded edges and is designed to rest upon a support surface such as a floor. A top 52 of the apparatus 10 includes a grate or perforated planar surface or platform 54 enabling a liquid spray or mist to pass therethrough. The platform including a grate 54 is supported on the bottom so as to support the weight of an average adult person. The platform 54 can be constructed of any durable material, such as metal or plastic. The platform 54 includes Velcro® pads 88 to secure a porous mat or textile to the top surface of the platform 54. Such porous mat or textile shall allow cleaning and sanitizing spray or mist to pass through, similar to the textile pads 42 and 44 of FIG. 1.

The apparatus 50 includes a beveled edge 56 which surrounds the outer perimeter of the top 52 of the platform 54. An on/off control switch 58 is located on top of the apparatus 50. A cover 60 covers a battery storage compartment. A dock 62 is included on the top 52 of the apparatus 50 for receiving a liquid storage container, such as an aerosol spray can 80 which is located within an aerosol can housing 66. The aerosol can housing 66 facilitates insertion and locking of the aerosol spray can 80 into the dock 62 of the apparatus 10. A cover 64 for the dock 62 is shown in the open position in FIG. 7. The aerosol can housing 66 for the aerosol can 80 is configured to be received by the dock 62. A slot or indention 51 in the surface of the display panel 53 housing lighting, such as LEDs 31 of FIG. 1, on the top 52 of the apparatus 50 that signal to a user the status of the apparatus 50 operation. The display panel 53 also indicates whether the contents of the aerosol can 66 include cleaning and sanitizing fluid for feet, footwear, or both.

Figure 7A:
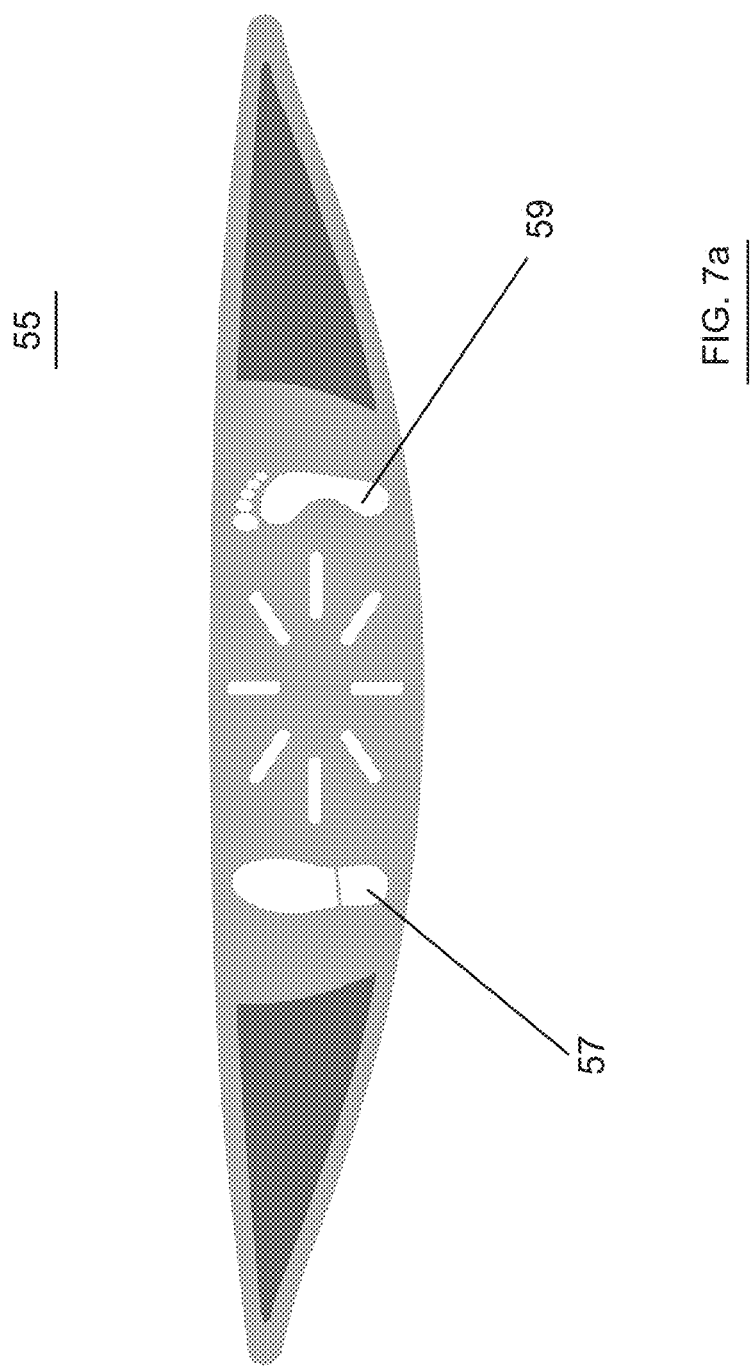
FIG. 7a is a top view of a display panel of the present invention.

FIG. 7a is a top view of a display membrane, transparent film or cover 55 for the display panel surface 53, wherein lighting located within the slot 51 can shine through. For example, if the apparatus detects cleaning fluid for footwear or shoes within the aerosol can 80, the image of a shoe 57 is illuminated to alert the user of the proper use for the cleaning fluid. If the apparatus 10 detects cleaning fluid for bare feet within the aerosol can 80, then the image of a bare foot 59 is illuminated to let the user know the proper use for the cleaning fluid.

FIG. 8 is a top view of the apparatus 50 shown in FIG. 7. Illustrated are the platform 54, beveled edge 56, dock cover 64, battery cover 60, and the on/off switch 58. Also illustrated are the aerosol can housing 66 for an aerosol can 80. The Velcro® pads 88 on top of the platform 54 are further illustrated.

FIG. 9 is a cross-sectional view of the apparatus 50 shown in and taken along line 9-9 of FIG. 8. Illustrated is the aerosol can housing 66 for an aerosol can 80 including a manifold 114 having a twist connector. The cover 64 for the dock 62 is shown in the raised position. The cover 64 is rotatably mounted to a base 70 of the apparatus 50 using a pair of hinges or pivotal mounts 68. The dock 62 illustrated in FIG. 8 is empty, exposing some of the internal components. A battery compartment 72 is shown housing batteries 84 and including the cover 60. Non-slip pads 74 on the bottom of the base 70 also are illustrated.

Figure 10:
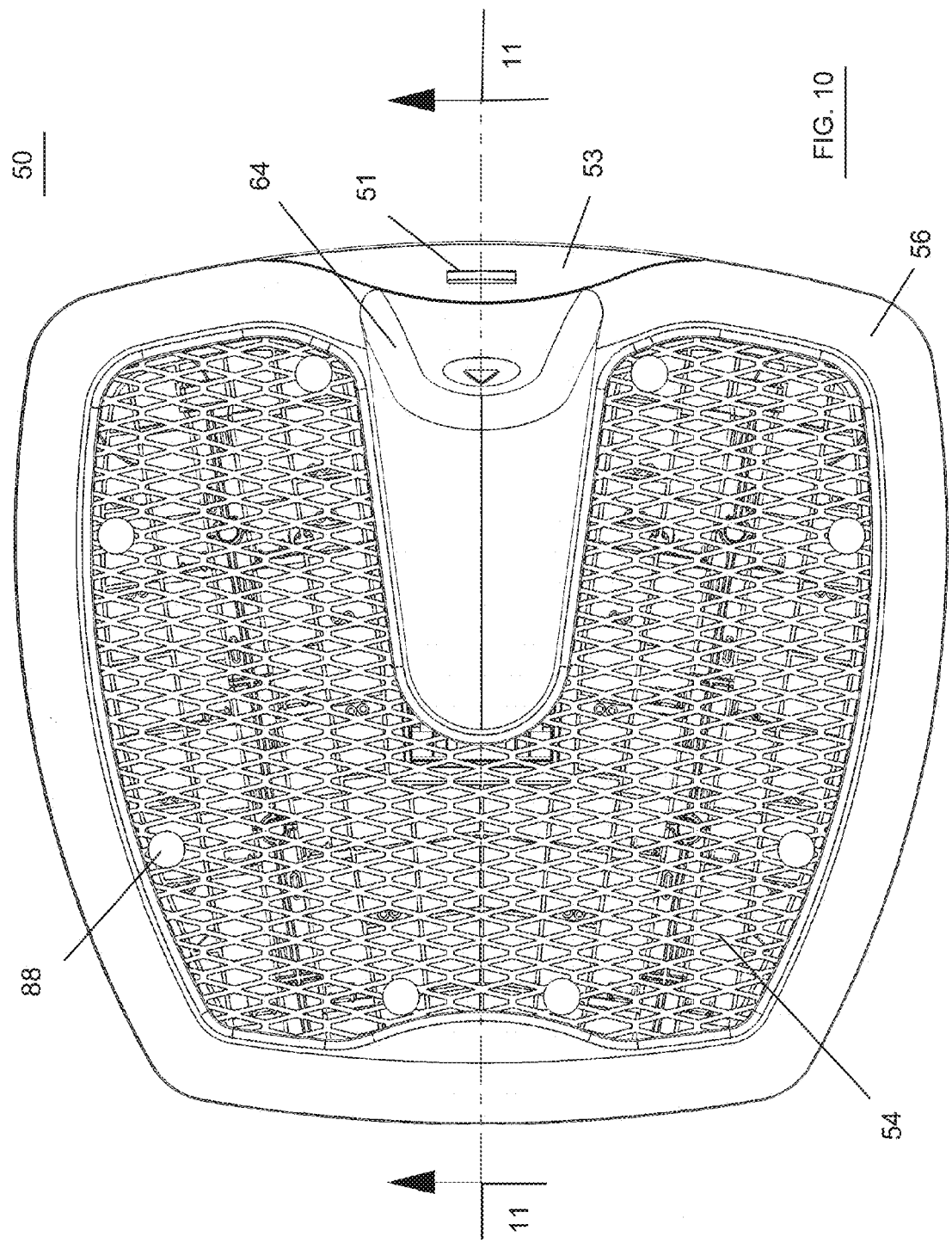
FIG. 10 is a plan view of the feet and footwear sanitizing and cleaning apparatus shown in FIG. 7, wherein the dock cover is in the closed position and the aerosol spray can is located within the dock.

FIG. 10 is a plan view of the apparatus 50 shown in FIGS. 7-9, wherein the dock cover 64 is in the closed position, and the aerosol can housing 66 containing an aerosol can is located within the dock 62. The platform 54, Velcro® pads 88, and beveled edge 56 also can clearly be seen.

Figure 11:
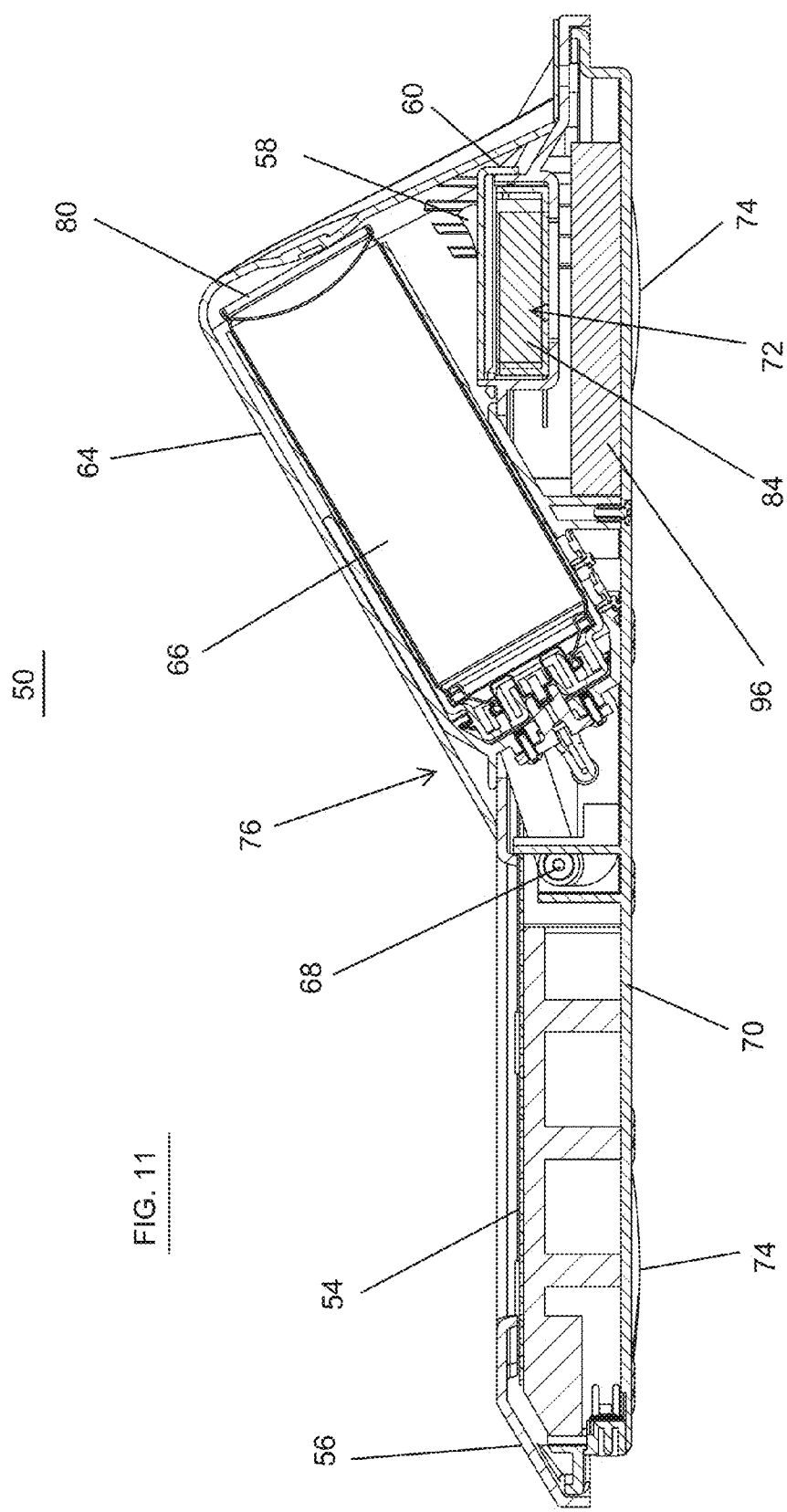
FIG. 11 is a cross-sectional view of the apparatus shown in and taken along line 11-11 of FIG. 10, and the aerosol can is located within the dock.

FIG. 11 is a cross-sectional view of the apparatus 50 shown in and taken along line 11-11 of FIG. 10. Illustrated is the housing 66 for an aerosol can 80 within the dock 62. An aerosol can 80 is located within the housing 66 and connected to a port 76 within the dock 62. The platform 54 is shown to be parallel to and below the upper surface of the beveled edge 56. The non-slip pads 74 are seen on the bottom of the base 70, and the batteries 84 are located within the battery receptacle 72. The on/off switch 58 and battery cover 60 are further illustrated. Also illustrated are the hinges 68 for the dock cover 64 and a control circuit 96 within the base 70.

Figure 12:
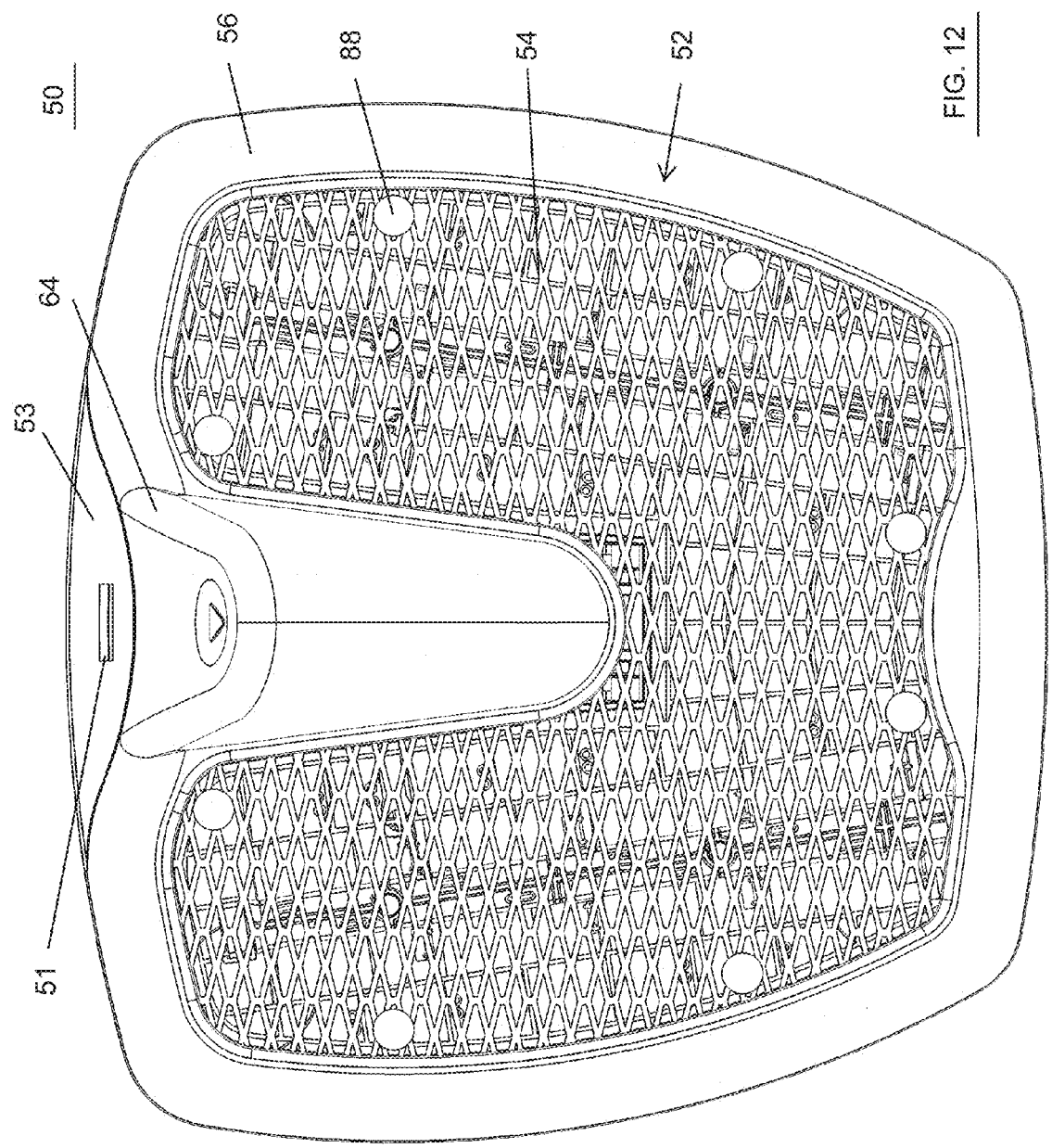
FIG. 12 is plan view of the feet and footwear sanitizing and cleaning apparatus shown in FIG. 10.

FIG. 12 is a plan view of the apparatus 50 shown in FIGS. 7-11. The dock cover 64 is in the closed position so as to cover the on/off switch 58 and battery compartment cover 60. The platform 54 is shown as well as the beveled edge 56. The panel display surface 53 and slot 51 for lighting sources also are illustrated.

Figure 13:
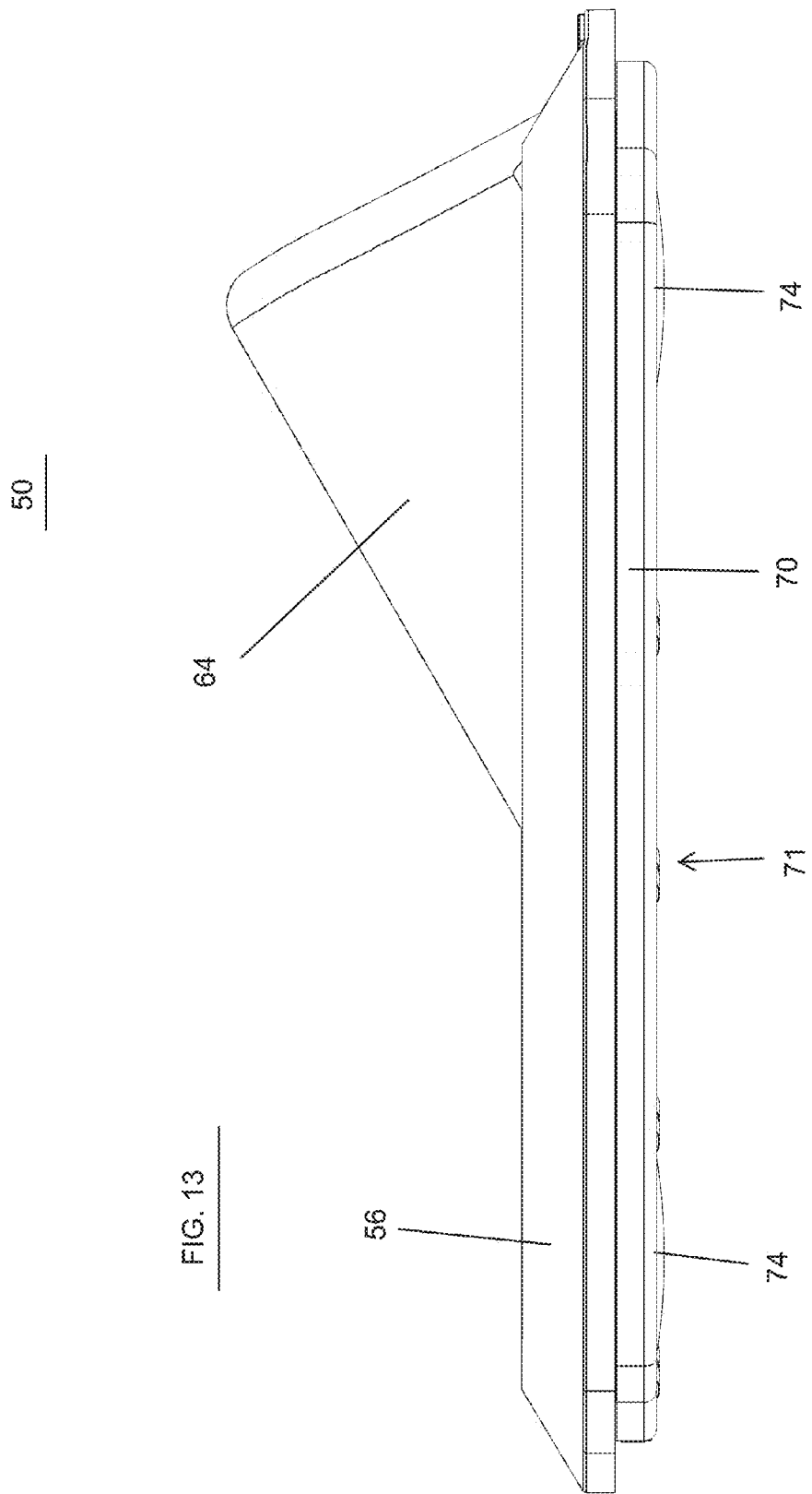
FIG. 13 is a side view of the feet and footwear sanitizing and cleaning apparatus shown in FIG. 12.

FIG. 13 is a side view of the apparatus 50 shown in FIG. 12. The dock cover, door, or hood 64 is shown in the closed position. In the closed position the dock hood 64 covers the battery compartment door 60 and the on/off switch 58. The beveled edge 56 is illustrated above the base 70, and the non-slip pads 74 are shown on the bottom 71 of the base 70.

Figure 14:
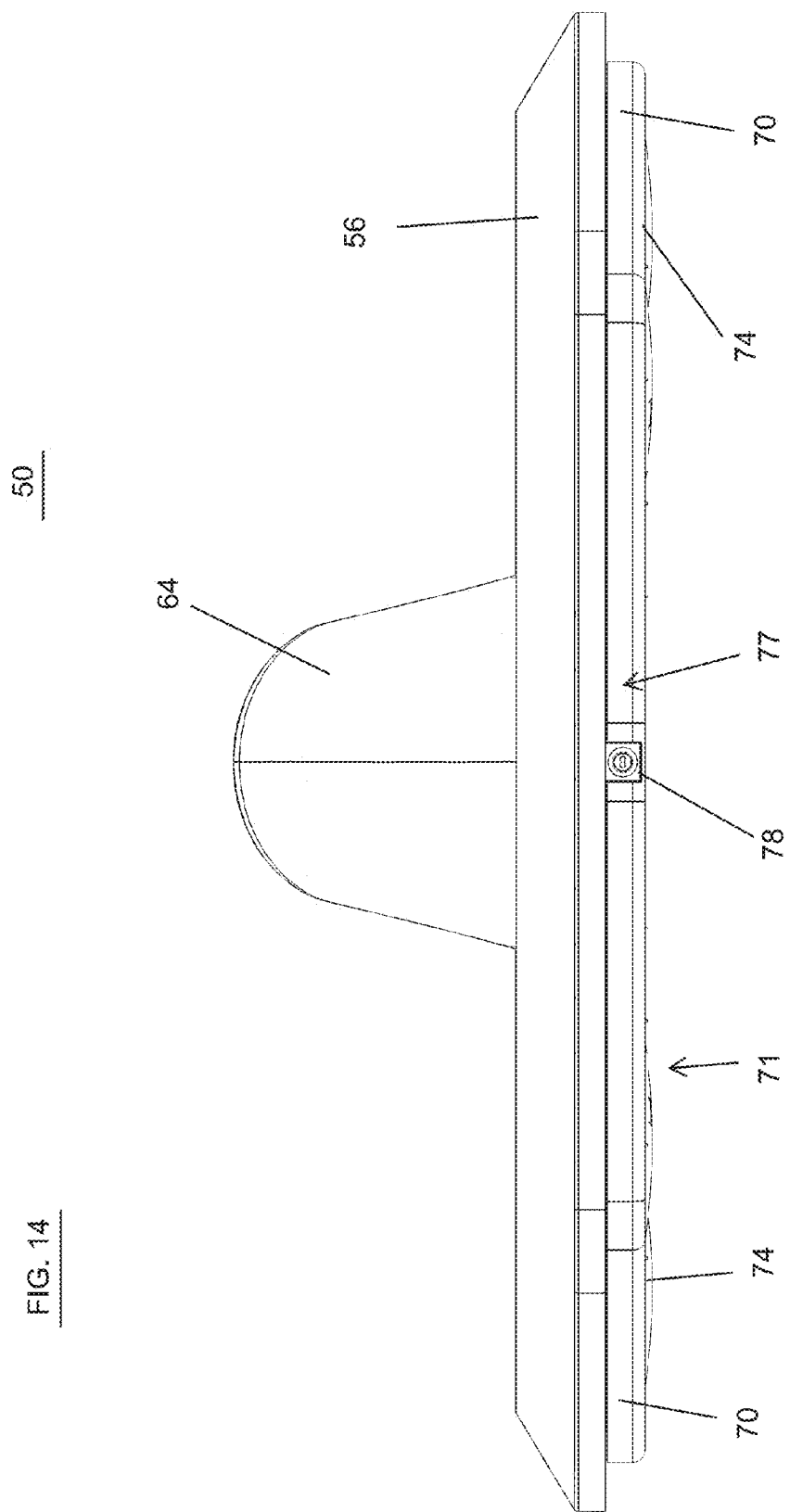
FIG. 14 is a rear view of the feet and footwear sanitizing and cleaning apparatus shown in FIG. 13.

FIG. 14 is a rear view of the apparatus 50 shown in FIG. 13. The dock cover 64 is shown in the closed position. The beveled edge 56 is illustrated above the base 70, and the non-slip pads 74 are shown on the bottom 71 of the base 70. A power supply and/or charging port 78 is located on the rear 77 of the base 70 of the apparatus 50.

Figure 15:
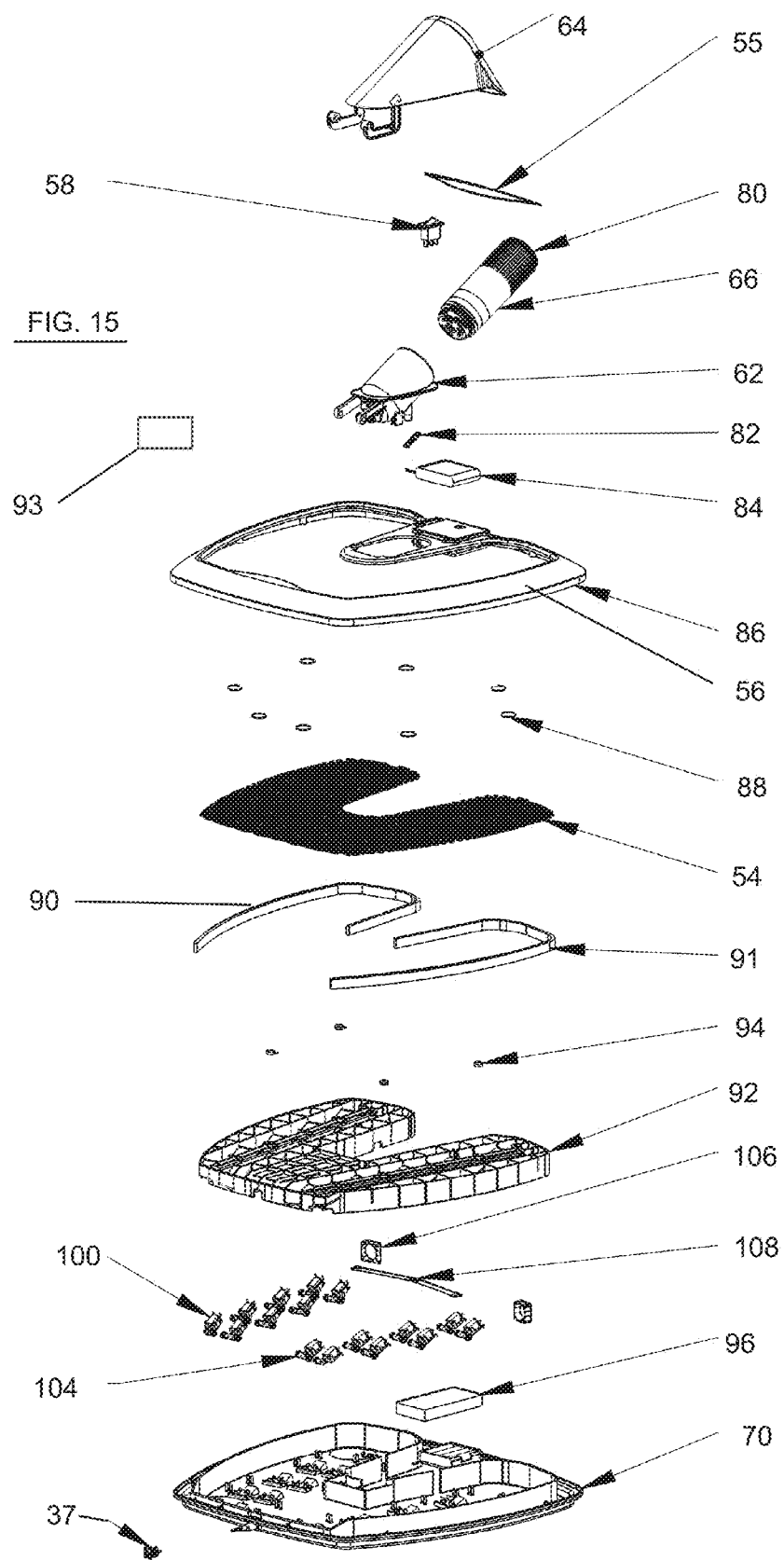
FIG. 15 is an exploded view of the apparatus shown in FIG. 7.

FIG. 15 is an exploded view of the apparatus 50 shown in FIGS. 7-14. The dock cover or hood 64 is shown at the top of FIG. 15, and a display membrane 55 and the on/off 58 is shown immediately below. The display membrane 55 covers the slot 51 and the display panel surface 53. The slot 51 contains lighting for a lighted display that functions to provide visual feedback to a user while apparatus 50 is operating. The lighting display, among other things, indicates to a user the contents of an aerosol can supplying cleaning and sanitizing fluid, as detected by a reflectance sensor 82 of the apparatus 50, such as whether the cleaning and sanitizing liquid contained within the aerosol can 80 is for cleaning feet, footwear, or both. An aerosol can 80 is shown in the aerosol can housing 66, along with the dock 62. An audio source or speaker 93 is shown below the dock 62 as part of the apparatus 10.

The reflectance sensor 82 is shown below the dock 62. The reflectance sensor 82 is preferably a QTR-1A reflectance sensor that carries a single infrared LED and phototransistor pair. The reflectance sensor 82 preferably is part number 2458 sold by Pololu. Other reflectance sensors can be used in the present invention which have the same functional capability. The reflectance sensor 82 preferably reads a visual code on the aerosol can housing 66 to determine the type of cleaning fluid contained within an aerosol can 80 that is currently inserted into the dock 62 of the apparatus 50.

A rechargeable battery 84 is located within the battery compartment 72 of the apparatus 50. The beveled edge 56 is shown to be part of the upper shell or top cover 86. The upper shell 86 also surrounds the battery compartment cover 60 and the dock 62. The platform 54 is shown below the upper shell 86, and the circular Velcro® pads 88 are included to be attached to the top of the platform 54 for securing a removable, replaceable and porous cover or mat. LED light strips 90 and 91 are located directly below the platform 54 and function to provide lighting for a user of the apparatus 50. The LED lighting strips 90, 91 preferably are model number 2547 sold by Pololu Corporation, 920 Pilot Road, Las Vegas, Nev. 89119.

Below the LED lighting strips 90, 91 is a compartmentalized support 92 for supporting the platform 54. Miniature vibration motors 94 are mounted within the compartmentalized support 92 and function to help remove particulates from footwear and feet and provide feedback to a user that apparatus 50 is operating by vibrating the platform 54. The compartmentalized support 92 is attached to the base 70.

The base 70 is located below the compartmentalized support 92. The base 70 is designed to rest on a floor or other supporting surface. The base 70 houses the batteries 84 within the battery compartment 72. A printed circuit board (PCB) or control circuit 96 containing a microprocessor and other necessary electronics to control and operate the apparatus 50 are contained within a PCB compartment 98 (FIG. 15*d*) of the base 70. Spray nozzles 100 including solenoid valves are mounted within brackets 102 inside the base 70. The spray nozzles 100 include plumbing connectors 104 to connect the spray nozzles 100 to the piping system or spray distribution system 107 (FIG. 15*d*) of the apparatus 50. The piping system 107 connects an aerosol can 80 within the dock 62 to all the spray nozzles 100. The solenoid valves included in the spray nozzles 100 preferably are model number ZHV-0414L sold by Zonhen Electric Appliances. The spray nozzles 100 are designed to function sequentially as cleaning liquid is pumped through the piping system 107. The control circuit 96 controls the sequential or other pattern of spraying of the spray nozzles 100.

Miniature fans 106 are included within the base 70. The miniature fans 106 function to facilitate removing and drying of sanitizing and cleaning liquid from the platform 54, and feet and shoes resting thereon. The miniature fans 106 are preferably model number 259-1557-ND sold by Digi-Key Corporation. Heating elements may be included with the fans 106 to improve drying capabilities. A weight sensor 108 is included within the base 70 to detect when a person is standing on the apparatus 50. The weight sensor 108 preferably is model number A201 sold by Tekscan, Inc. The PCB or controller 96 and power port 37 also are illustrated at the bottom of FIG. 15.

FIGS. 15*a*-15*d* are enlarged sections of the elements shown in FIG. 15 of the preferred embodiment of the present invention. FIG. 15*a* shows the dock cover 64. Arms 110,111 extend from a back 109 of the dock cover 64 to pivotally mount the dock cover 64 via pivot mounts 112,113 at ends of the arms 110,111. FIG. 15*b* provides an enlarged view of the on/off switch 58 and the display membrane 55. The display membrane 55 covers the panel display surface 53 and slot 51 of the apparatus 50 and includes labeling for the visual and lighted display. The aerosol can housing 66 containing an aerosol can 80 and the dock 62 also are shown in FIG. 15*b*.

The bottom of the aerosol can 80 can be seen extending from the aerosol can housing 66. The nozzle 115 of the aerosol can be seen extending through the manifold 114 having a twist-lock for securing the aerosol can housing 66 within the dock 62. Slanted ridges 118 on the manifold 114 on the side of the top 117 of the housing 66 are designed to twist and secure the aerosol can housing 66 within the dock 62. The reflectance sensors 82 are located below the dock 62 to determine the type of aerosol can 80 located within the housing 66; such as for shoes or bare feet. The aerosol can housing 66 includes a visual label to be detected by the reflectance sensors 82 to indicate the contents of the aerosol spray can 80.

FIG. 15*c* illustrates an enlarged view of the top cover 86 of the apparatus 50. The top cover 86 includes the beveled edge 56, and opening 120 as a receptacle for shoes and feet. An aperture 122 in the top cover 86 is shaped for receiving the dock 62, and an aperture 124 is configured for receiving the on/off switch 58. The battery compartment 72 is formed within the top cover 86, as is the battery compartment cover 60. The batteries 84 to be stored within the battery compartment 72 can be replaceable or rechargeable. Also shown in FIG. 15*c* are enlarged views of the Velcro® disk 88, platform 54, and LED lighting strips 90,91.

FIG. 15*d* provides an enlarged view of the miniature vibrations motors 94 and the compartmentalized support 92. The miniature fans 106 and weight sensor 108 are shown in an enlarged view. Enlarged views of the spray nozzles and solenoid valves 100 and the plumbing connectors 104 are shown in FIG. 15*d*. The spray nozzles and solenoid valves 100 are mounted within the brackets 102 on the base 70. A piping network 107 connects the plumbing connectors 104 to the spray output 115 (FIG. 16) of the aerosol can 80. The PCB 96 fits into the PCB compartment 98 of the base 70. The battery compartment 72 in the base 70 houses the batteries 84. An AC connector 126 for charging the batteries 84 is shown located on the front of the base 70.

Figure 16:
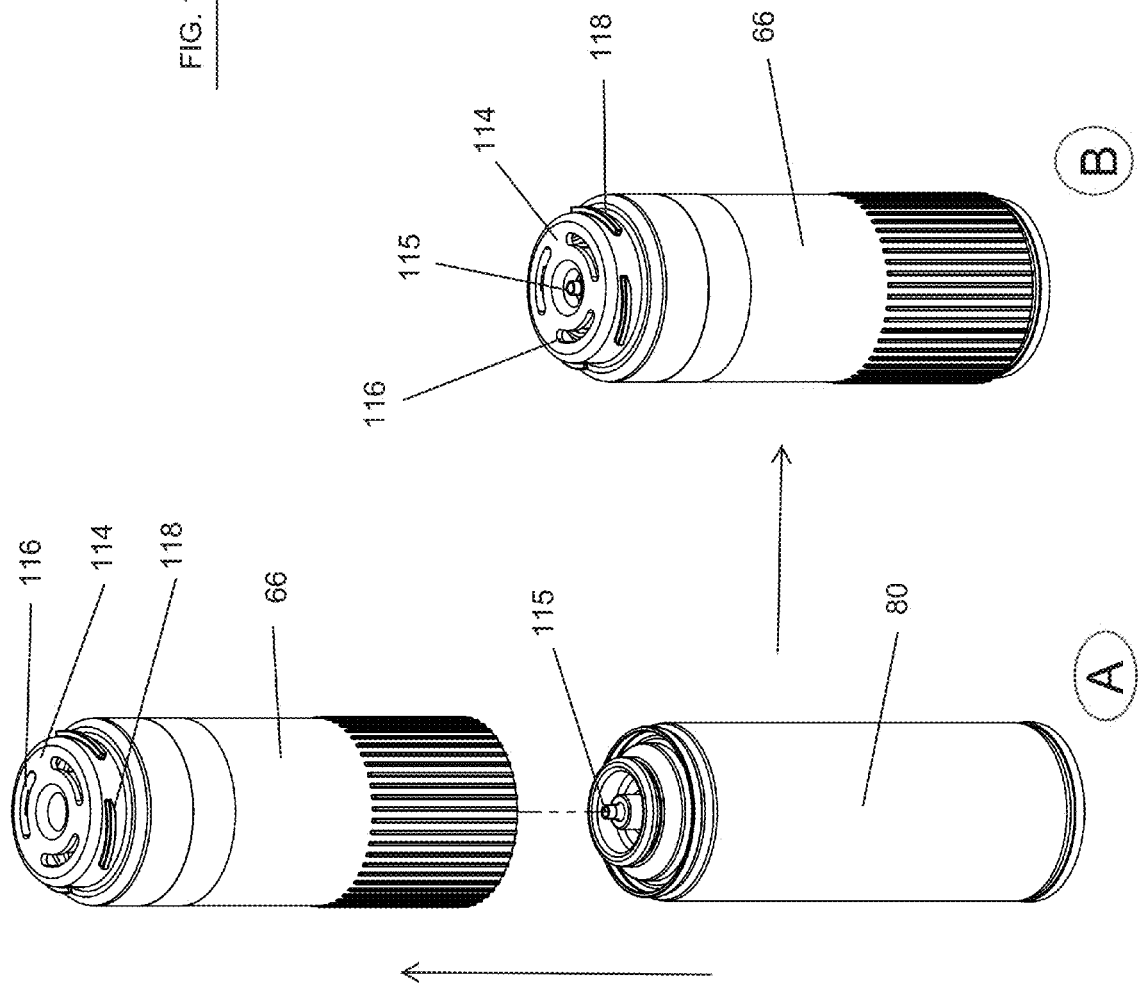
FIG. 16 is an enlarged view of the aerosol spray can and aerosol can housing shown in FIG. 7.

FIG. 16 is an enlarged view of the aerosol can 80 and the aerosol can housing 66. In view "A" of FIG. 16 the aerosol can 80 is about to be inserted into the rear of the aerosol can housing 66. After the aerosol can 80 is inserted into the aerosol can housing 66, the aerosol can 80 within the aerosol can housing 66 has the configuration shown in view "B" of FIG. 16. The manifold 114 and the ridges 118 are shown for securing the housing 66 within the dock 62 when the housing 66 is twisted to lock the housing 66 within the dock 62. The nozzle 115 on the aerosol can 80 also is illustrated.

Figure 17:
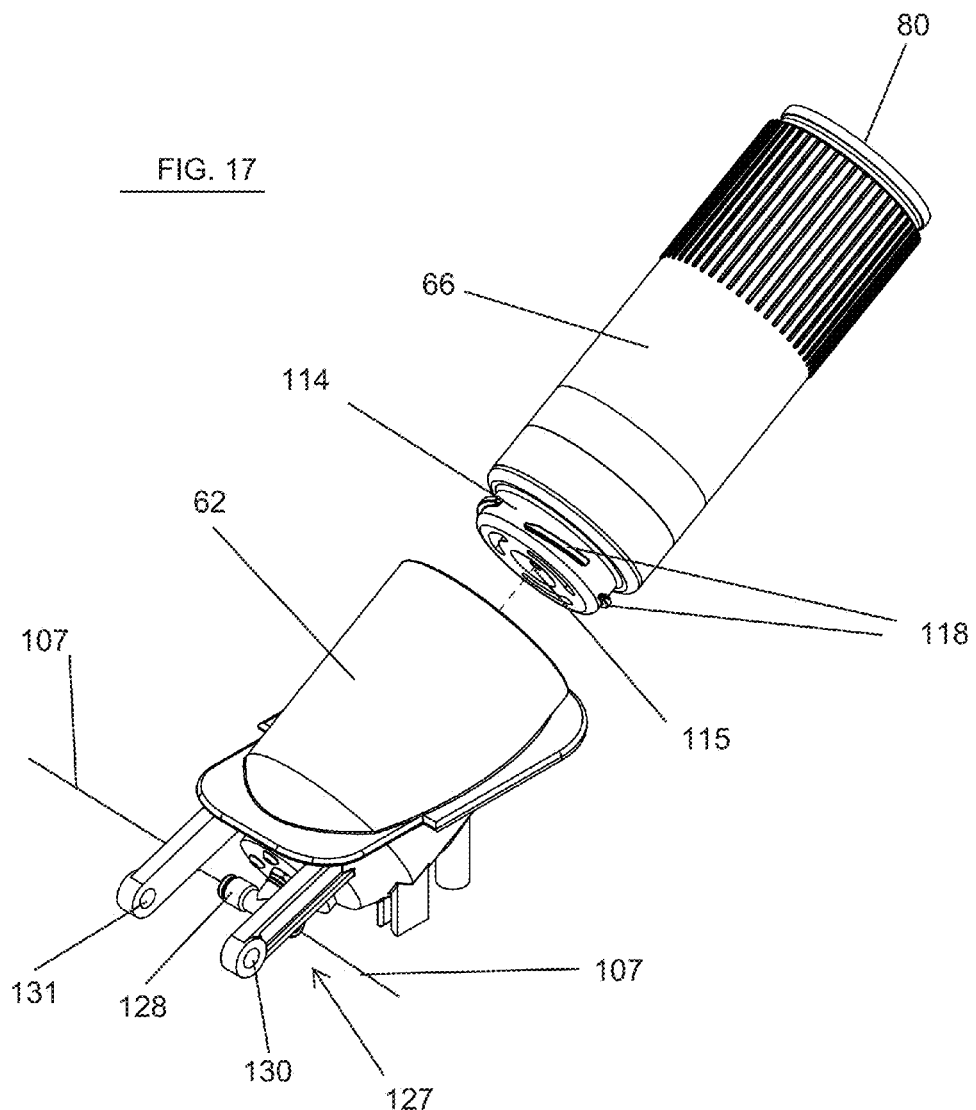
FIG. 17 is an enlarged view of the aerosol spray can, aerosol can housing, and dock of FIG. 7.

FIG. 17 is an enlarged view of the dock 62 and the aerosol can housing 66 containing an aerosol can 80 therein. The rear 127 of the dock 62 includes piping connectors 128 for communicating the nozzle 115 of the aerosol spray can 80 to the piping network 107 and the spray nozzles and solenoid valves 100 attached to the base 70. Arms 130,131 secure the dock 62 to the base 70. The ridges 118 on the manifold 114 for securing the housing 66 within the dock 62 also can be seen.

Figure 18:
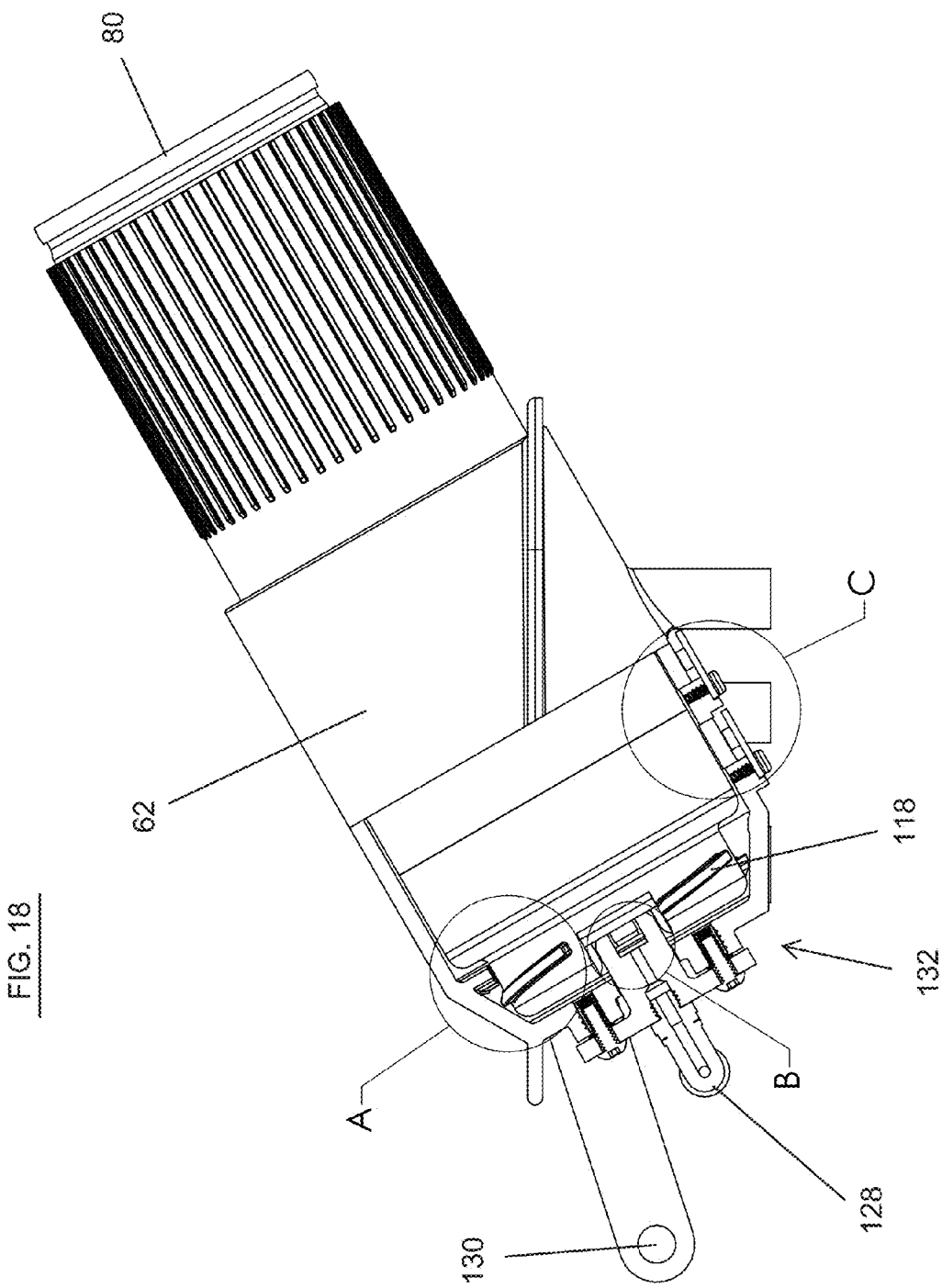
FIG. 18 is enlarged cross-sectional view of the dock and the aerosol can housing shown in FIG. 7.

FIG. 18 shows a cross-section view of the connecting mechanism of the dock 62. The mounting arm 130 and piping connectors 128 are shown. FIG. 18 includes circled or highlighted portions "A," "B," and "C." Each of these portions are discussed in more detail in FIGS. 19-21, respectively.

Figure 19:
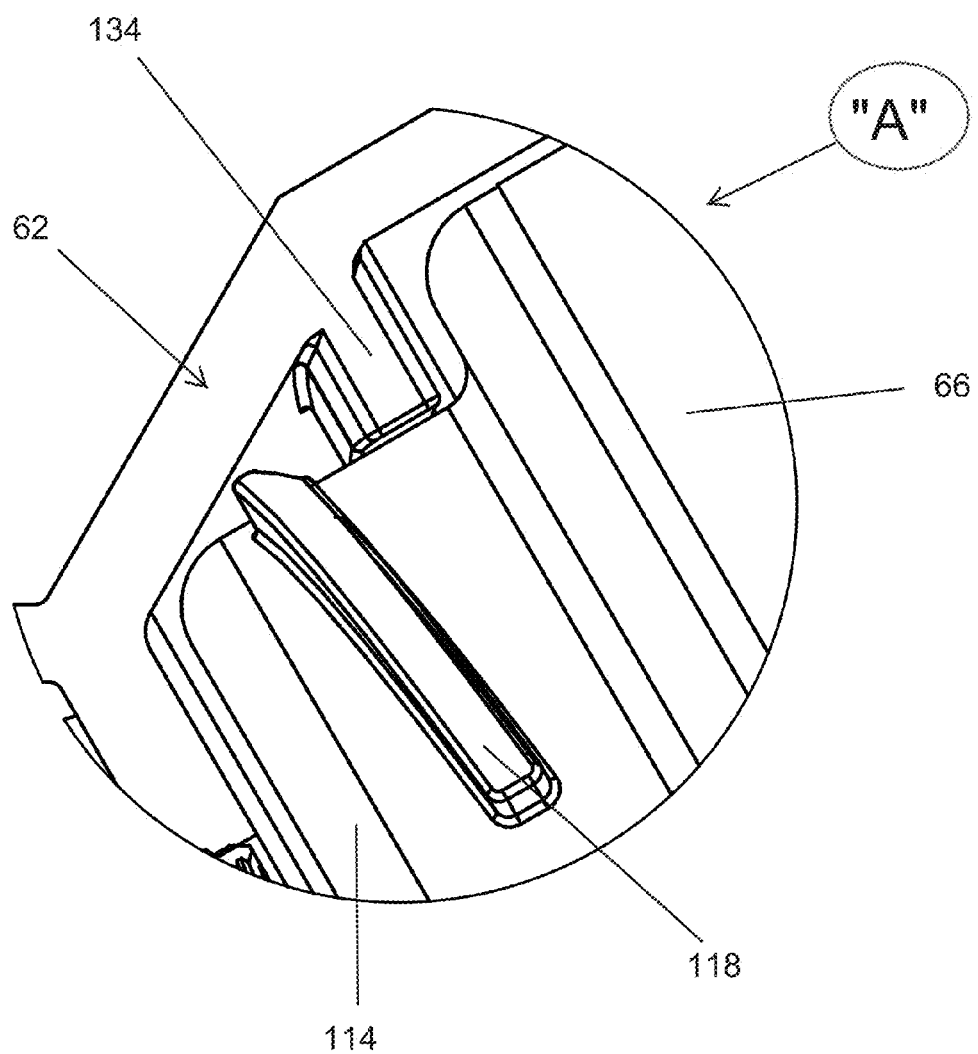
FIG. 19 is an enlarged view of circled portion "A" shown in FIG. 18.

FIG. 19 is an enlarged view of portion "A" shown in FIG. 18. FIG. 19 is an enlarged view of the twist connector having ridges 118 on the manifold 114 of the aerosol can housing 66. The twist connector includes curved ridges 118 that lock tightly against ridges 134 on the inside of the dock 62 when the housing 66 is twisted in place.

Figure 20:
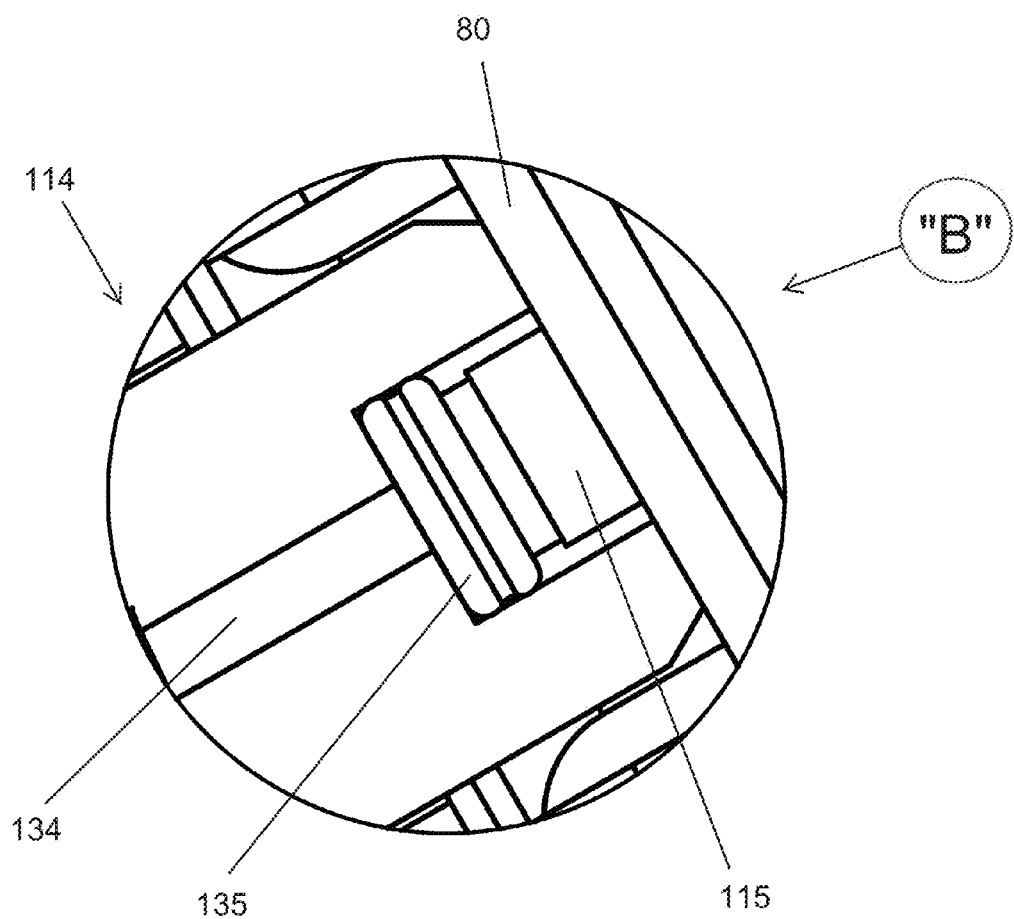
FIG. 20 is an enlarged view of circled portion "B" shown in FIG. 18.

FIG. 20 is an enlarged view of portion "B" shown in FIG. 18. FIG. 20 shows an enlarged view of the manifold 114 connecting the nozzle 115 of the aerosol can 80 to the piping system 134 in the manifold 114 for distributing the sanitizing solution to the spray nozzles 100 on the base 70. The manifold 114 includes a press plate 135 for pressing down on the nozzle 115 of the aerosol spray can 80 and opening the valve on the aerosol spray can 80 for releasing the sanitizing fluid contents therein to the piping system 107 of the apparatus 50.

Figure 21:
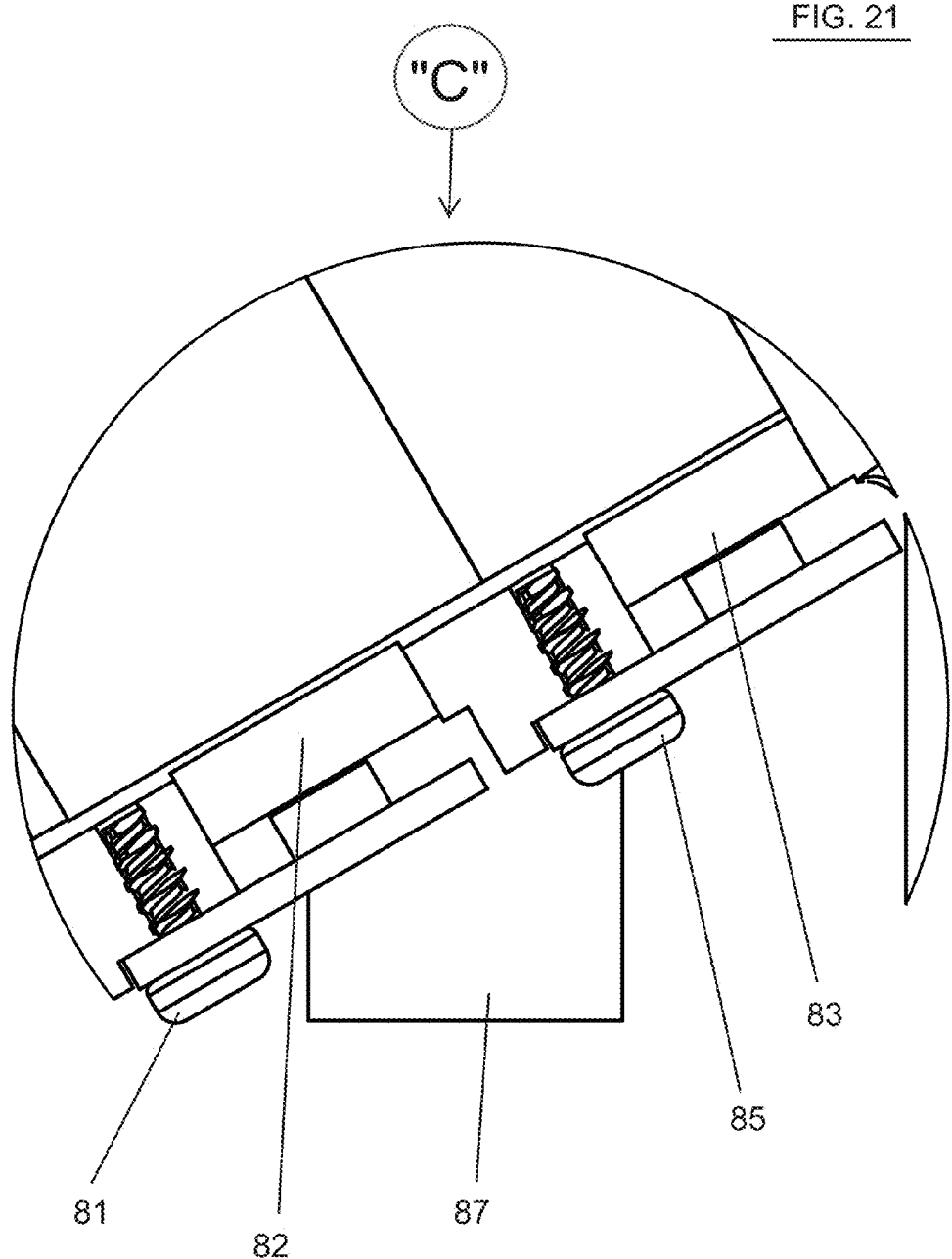
FIG. 21 is an enlarged view of circled portion "C" shown in FIG. 18.

FIG. 21 is an enlarged view of the portion "C" shown in FIG. 18. FIG. 21 shows the optical sensors 82,83 mounted within the dock 62. The two color optical sensors 82,83 are mounted within the dock 62 using screws 81,85, respectively. The dock 62 is supported by a bracket 87. When the aerosol can housing 66 is installed in the dock 62, colored areas on the aerosol can housing 66 align with the sensors 82,83. The first sensor 82 can detect whether a housing 66 is present. If the housing 66 is present, the second sensor 83 detects which type cleaning fluid is within the aerosol can 80 (foot or shoe sanitizer). Alternatively, the each sensor 83 and 83 reads a visual code on the aerosol can housing 66, thus increasing the available number of detected content options of an aerosol can 80 (such as four content options if two sensors can each detect at least two codes or colors). The same functionality could be accomplished with other types of sensors and/or switches. If the apparatus 50 were used with only one type of aerosol can, such as one sanitizer for both shoes and feet, this functionality would not be necessary. Alternatively, the optical sensors 82,82 could detect a code on the aerosol can 80 to determine if cleaning and sanitizing fluid contained within the aerosol can 80 is for feet, shoes, or both. The controller 96 would then display the appropriate visual display via lighting in the slot 51 to indicate to a user the aerosol can 80 contents.

Figure 22:
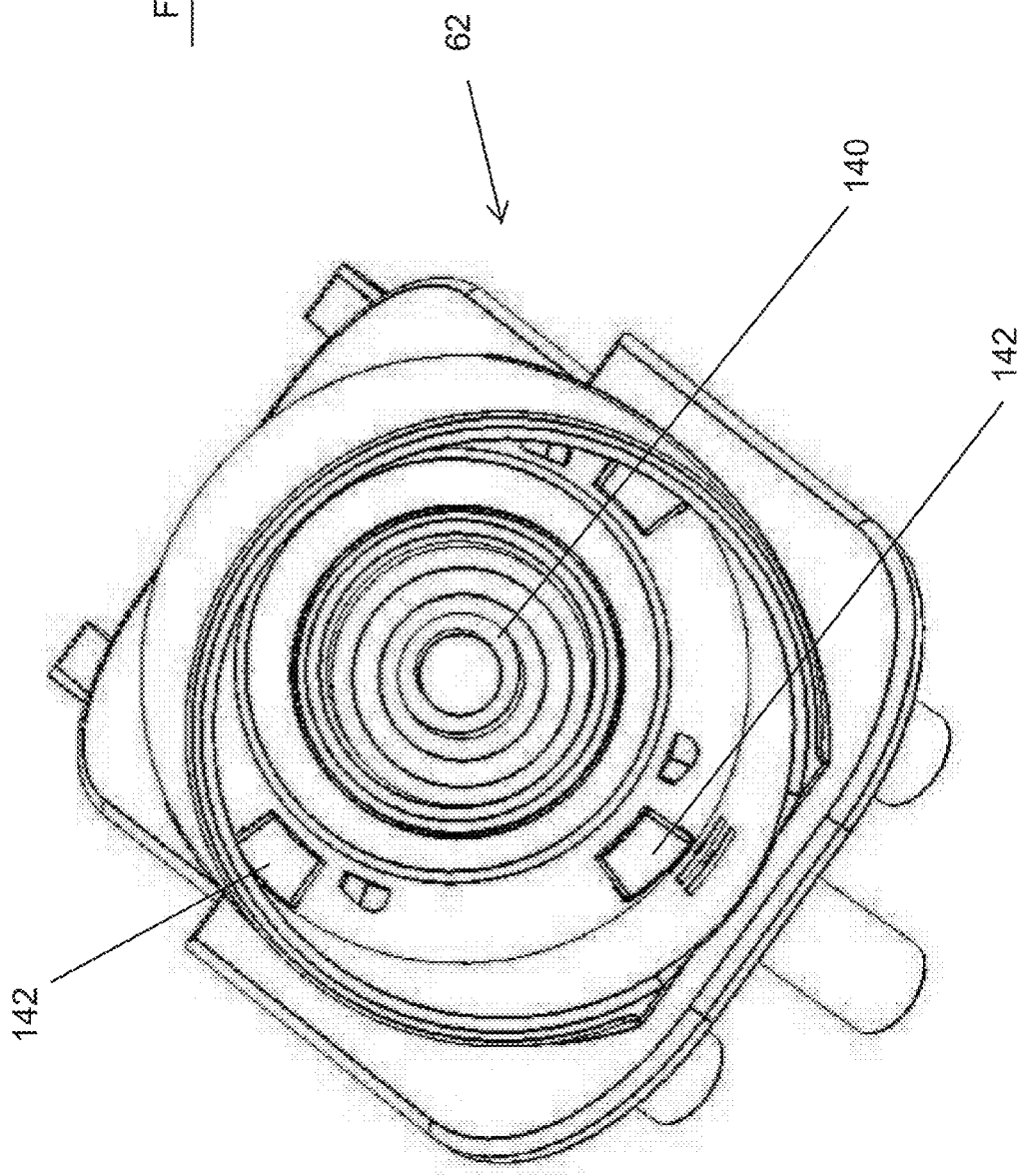
FIG. 22 is a perspective view of inside of the dock.

FIG. 22 is an enlarged view of the inside of the dock 62. Inside the dock 62 an O-ring 140 can been seen for receiving the nozzle 115 of an aerosol can 80. Also illustrated are extensions 142 for securing the manifold 114 of the housing 66 within the dock 62. When the ridges 118 of the manifold 114 are twisted or rotated under the extensions 142 within the dock 62, the housing 66 is secured within the dock 62.

Figure 23:
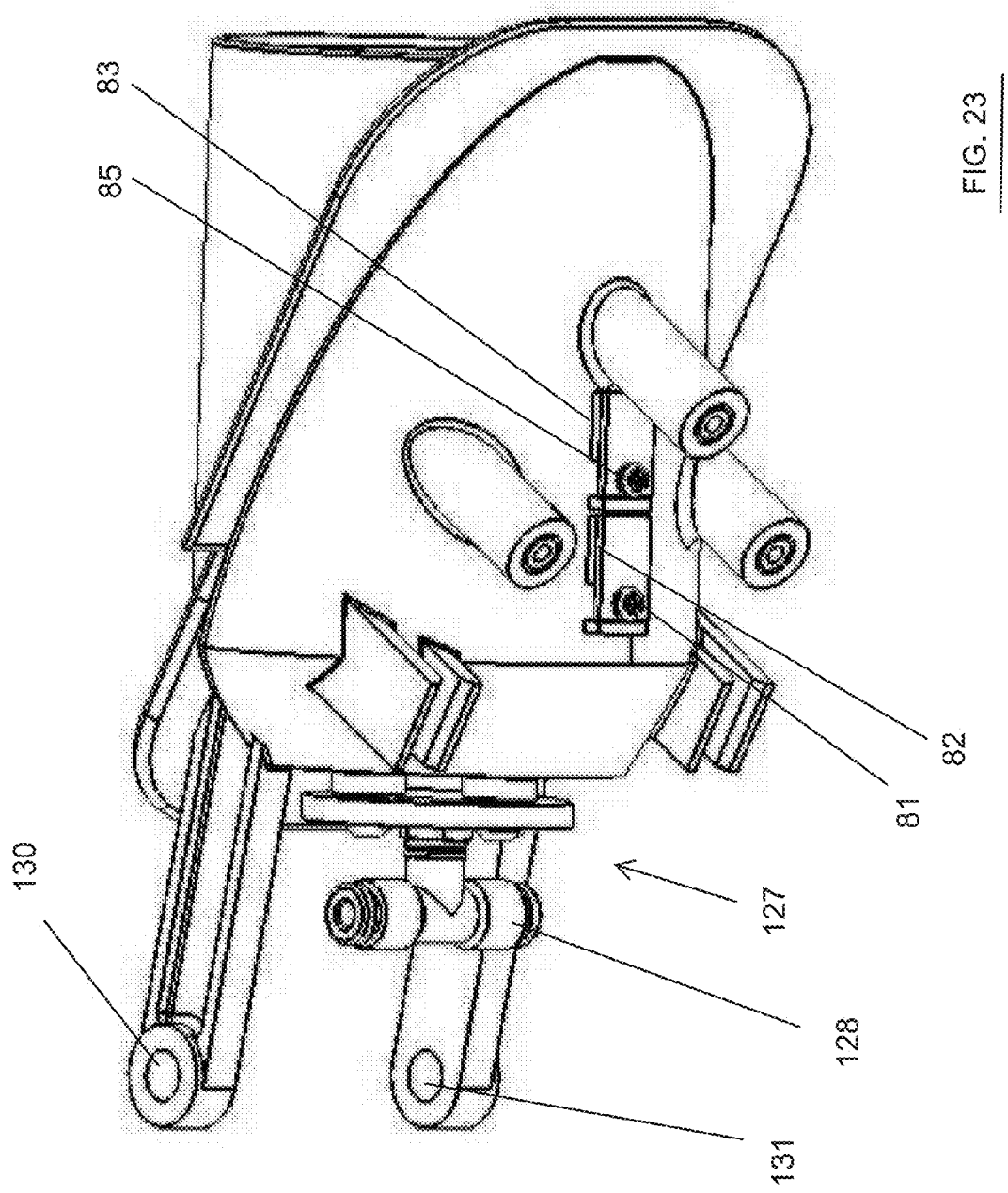
FIG. 23 is a perspective view of the outside of the dock illustrating optical sensors.

FIG. 23 illustrates the underside of the dock 62. Illustrated are the screws 81 and 85 for securing the optical sensors 82 and 83, respectively. Further illustrated are the mounting arms 130 and 131 and the piping connectors 128 are the rear 127 of the dock 62.

Figure 24:
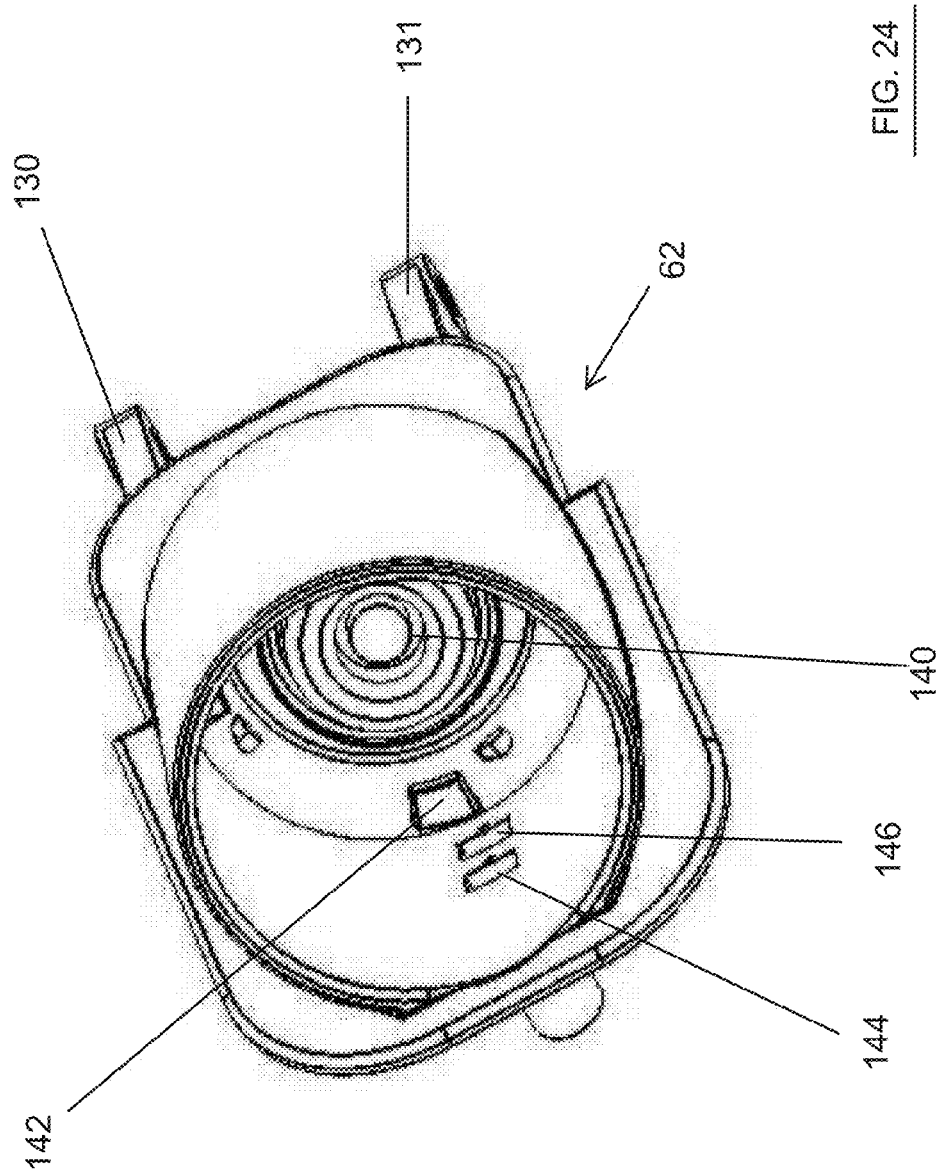
FIG. 24 is an internal view of the dock illustrating apertures for the optical sensors.

FIG. 24 is an internal view of the dock 62 from a different perspective that FIG. 22. In FIG. 24 apertures 144 and 146 in the dock 62 can be seen. These apertures 144 and 146 enable the optical sensors 82 and 83 on the bottom of the dock 62 to scan a visual code or label on an aerosol can 80. The extensions 142 and the O-ring 140 also can be seen in the dock 62.

Figure 25:
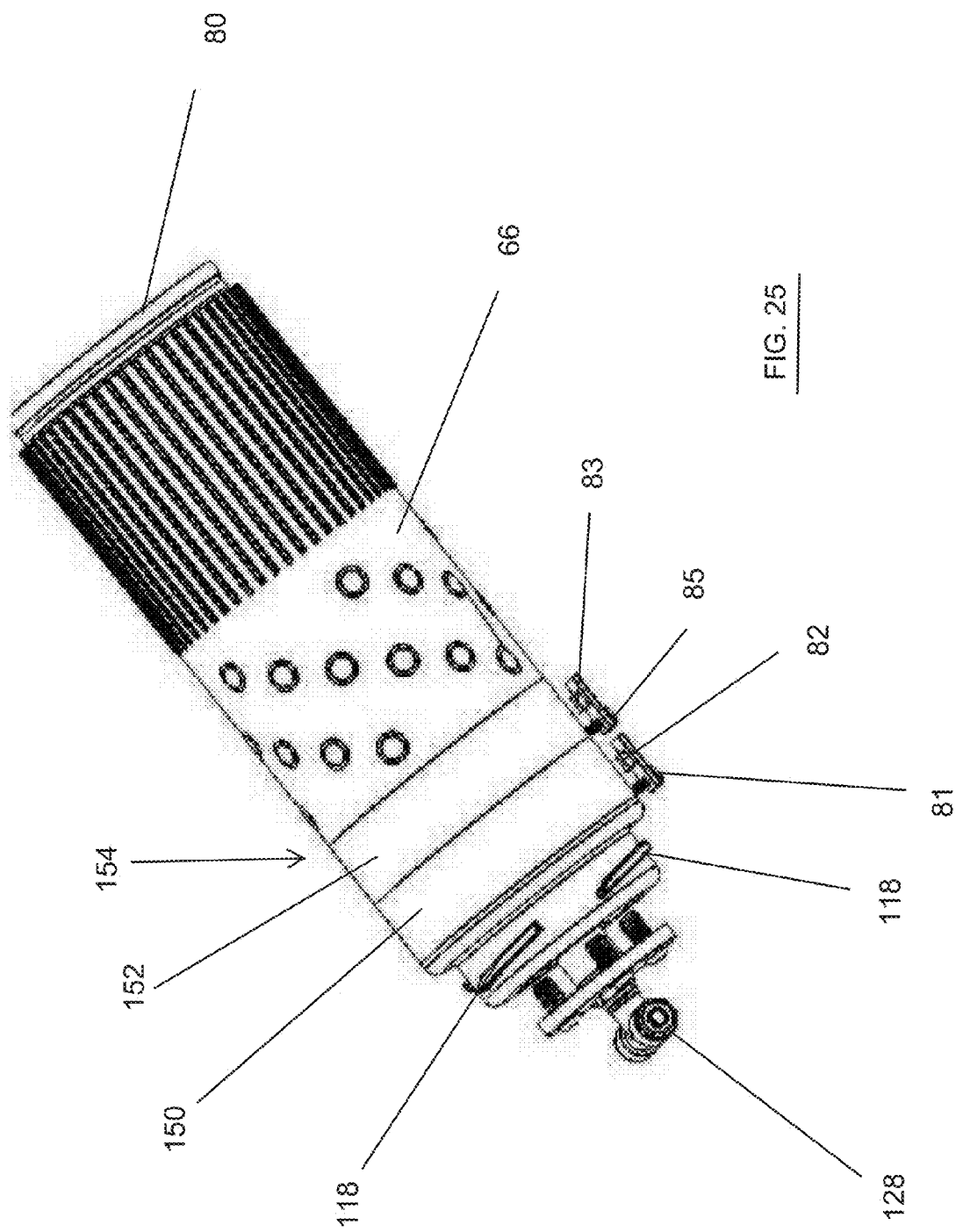
FIG. 25 illustrates visual code labels on an aerosol can housing.

FIG. 25 illustrated visual label codes or bands 150 and 152 near the top 154 of the aerosol can housing 66. The visual codes or bands 150 and 152 are preferably on the aerosol can housing 66, but can be on the aerosol can 80 in other embodiments. Similarly, the visual codes bands 150 and 152 can be different colors, or bar codes, or other known visual codes to be detected by the optical sensors 82 and 83. The visual sensors 82 and 83 read the optical codes bands or other visual markings and send appropriate electrical signals to the controller 96. The controller 96 determines the contents of an aerosol can 80 by looking up the scanned visual codes from a look up table or similar storage format, and then displays a visual image on the visual indicator in slot 51 to alert a user as to the type of cleaning and sanitizing solution within the aerosol can 80.

While specific embodiments have been shown and described to point out fundamental and novel features of the invention as applied to the preferred embodiments, it will be understood that various omissions and substitutions and changes of the form and details of the invention illustrated and in the operation may be done by those skilled in the art, without departing from the spirit of the invention.

The invention claimed is:

1. An apparatus for automatically cleaning soles of both feet and footwear, comprising:
   a base;
   a platform located above the base having a top surface and a bottom surface, and the platform enables liquid to pass therethrough;
   a dock connected to the platform and having an input sized for receiving a nozzle of an aerosol can;
   a plurality of spray nozzles located below the platform and configured to direct liquid from below the bottom surface, through the platform, to the top surface;
   a piping network connecting the input of the dock to the plurality of spray nozzles, thereby enabling contents of an aerosol can connected to the input of the dock to flow through the piping network and out the plurality of spray nozzles;
   a control circuit for controlling output operation of the plurality of spray nozzles; and
   an optical sensor connected to the dock for reading an optical code on an aerosol can to be located within the dock to determine contents of an aerosol can within the dock.

2. The apparatus of claim 1, further comprising:
   an aerosol can located within the dock, wherein a nozzle of the aerosol can is connected to the input of the dock.

3. The apparatus of claim 1, wherein the platform includes a grate.

4. The apparatus of claim 1, further comprising:
a vibration source connected to and for vibrating the platform.

5. The apparatus of claim 1, further comprising:
a rechargeable power source.

6. The apparatus of claim 1, further comprising:
a porous surface material located on top of the platform for absorbing liquid.

7. The apparatus of claim 1, further comprising:
a fan connected to and for circulating air through the platform.

8. The apparatus of claim 1, further comprising:
a weight sensor connected to the control circuit for detecting when a person steps onto the platform.

9. The apparatus of claim 1, further comprising:
a housing for housing an aerosol can and securing an aerosol can within the dock.

10. The apparatus of claim 1, wherein the optical sensor is a barcode scanner further comprising:
a sensor plate for activating the apparatus.

11. The apparatus of claim 9, wherein the housing contains an aerosol can.

12. The apparatus of claim 1, further comprising:
a housing for receiving an aerosol can, wherein the housing is to be inserted into the dock; and
an aerosol can within the housing.

13. The apparatus of claim 9, further comprising:
a manifold on the housing for securing the housing within the dock.

14. The apparatus of claim 13, wherein the manifold has a circular configuration.

15. The apparatus of claim 13, further comprising:
slanted ridges on the manifold enabling the manifold to be secured within the dock by rotating the manifold.

16. The apparatus of claim 1, further comprising:
a dock cover rotatably connected to the dock.

17. The apparatus of claim 1, further comprising:
a plurality of miniature fans connected to and for circulating air through the platform.

18. The apparatus of claim 1, further comprising:
a compartmentalized support below and supporting the platform.

19. An apparatus for automatically cleaning soles of both feet and footwear, comprising:
a base;
a platform located above the base having a top surface and a bottom surface, and the platform enables liquid to pass therethrough;
a dock connected to the platform and having an input sized for receiving a nozzle of an aerosol can;
a plurality of spray nozzles located below the platform and configured to direct liquid from below the bottom surface, through the platform, to the top surface;
a piping network connecting the input of the dock to the plurality of spray nozzles, thereby enabling contents of an aerosol can connected to the input of the dock to flow through the piping network and out the plurality of spray nozzles;
a housing for receiving an aerosol can, wherein the housing is to be inserted into the dock;
a manifold on the housing for securing the housing within the dock; and
an aerosol can within the housing, wherein a nozzle of the aerosol can is connected to the input of the dock.

20. An apparatus for automatically cleaning soles of both feet and footwear, comprising:
a base;
a platform located above the base having a top surface and a bottom surface, and the platform enables liquid to pass therethrough;
a dock connected to the platform and having an input sized for receiving a nozzle of an aerosol can;
a plurality of spray nozzles located below the platform and configured to direct liquid from below the bottom surface, through the platform, to the top surface; and
a piping network connecting the input of the dock to the plurality of spray nozzles, thereby enabling contents of an aerosol can connected to the input of the dock to flow through the piping network and out the plurality of spray nozzles.

* * * * *